(12) United States Patent
Weydt et al.

(10) Patent No.: US 11,710,562 B2
(45) Date of Patent: Jul. 25, 2023

(54) GESTURE-BASED CONTROL OF DIABETES THERAPY

(71) Applicant: Medtronic MiniMed, Inc., Northridge, CA (US)

(72) Inventors: Patrick E. Weydt, Moorpark, CA (US); Pratik J. Agrawal, Porter Ranch, CA (US); Louis J. Lintereur, Stevenson Ranch, CA (US); Lavie Golenberg, Bloomfield Hills, MI (US); David Dunleavy, West Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 499 days.

(21) Appl. No.: 17/004,969

(22) Filed: Aug. 27, 2020

(65) Prior Publication Data
US 2021/0060247 A1  Mar. 4, 2021

Related U.S. Application Data

(60) Provisional application No. 62/893,722, filed on Aug. 29, 2019, provisional application No. 62/893,717, filed on Aug. 29, 2019.

(51) Int. Cl.
*G16H 40/67* (2018.01)
*G16H 20/17* (2018.01)
(Continued)

(52) U.S. Cl.
CPC ......... *G16H 40/67* (2018.01); *A61B 5/14532* (2013.01); *A61B 5/7405* (2013.01);
(Continued)

(58) Field of Classification Search
None
See application file for complete search history.

(56) References Cited

U.S. PATENT DOCUMENTS

| 7,935,076 B2 | 5/2011 | Estes et al. |
| 9,008,803 B2 | 4/2015 | Blomquist |

(Continued)

FOREIGN PATENT DOCUMENTS

| EP | 3417773 A1 | 12/2018 |
| KR | 20180028823 A | 3/2018 |

(Continued)

OTHER PUBLICATIONS

Castle et el., "Future of Automated Insulin Delivery Systems," Diabetes Technology & Therapeutics, vol. 19, Supplement 3, Jun. 1, 2017, 6 pp.

(Continued)

*Primary Examiner* — Manuel A Mendez
(74) *Attorney, Agent, or Firm* — Weaver Austin Villeneuve & Sampson LLP

(57) ABSTRACT

Devices, systems, and techniques for controlling delivery of therapy for diabetes are described. In one example, a system includes a wearable device configured to generate user activity data associated with an arm of a user; and one or more processors configured to: identify at least one gesture indicative of utilization of an injection device for preparation of an insulin injection based on the user activity data; based on the at least one identified gesture, generate information indicative of at least one of an amount or type of insulin dosage in the insulin injection by the injection device; compare the generated information to a criteria of a proper insulin injection; and output information indicative of whether the criteria is satisfied based on the comparison.

20 Claims, 8 Drawing Sheets

(51) Int. Cl.

| | |
|---|---|
| *G06F 3/01* | (2006.01) |
| *H04W 4/02* | (2018.01) |
| *A61B 5/145* | (2006.01) |
| *A61B 5/00* | (2006.01) |
| *A61M 5/142* | (2006.01) |
| *G16H 40/20* | (2018.01) |
| *G16H 70/40* | (2018.01) |
| *A61K 38/28* | (2006.01) |
| *A61M 5/172* | (2006.01) |
| *G16H 20/60* | (2018.01) |
| *G06N 3/08* | (2023.01) |

(52) U.S. Cl.
CPC .............. *A61B 5/746* (2013.01); *A61K 38/28* (2013.01); *A61M 5/14244* (2013.01); *A61M 5/14248* (2013.01); *A61M 5/1723* (2013.01); *G06F 3/017* (2013.01); *G06N 3/08* (2013.01); *G16H 20/17* (2018.01); *G16H 20/60* (2018.01); *G16H 40/20* (2018.01); *G16H 70/40* (2018.01); *H04W 4/027* (2013.01); *A61M 2205/3584* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2230/201* (2013.01); *A61M 2230/63* (2013.01)

(56) References Cited

U.S. PATENT DOCUMENTS

| | | | |
|---|---|---|---|
| 10,080,840 | B2 | 9/2018 | Gescheit et al. |
| 10,258,745 | B2 | 4/2019 | Despa et al. |
| 10,307,538 | B2 | 6/2019 | Desborough et al. |
| 2014/0315162 | A1 | 10/2014 | Ehrenkranz |
| 2015/0246179 | A1 | 9/2015 | Zur et al. |
| 2016/0306932 | A1 | 10/2016 | Fateh et al. |
| 2017/0189625 | A1 | 7/2017 | Cirillo et al. |
| 2017/0228518 | A1 | 8/2017 | Booth et al. |
| 2017/0249445 | A1 | 8/2017 | Devries et al. |
| 2018/0147362 | A1 | 5/2018 | Arenas Latorre et al. |
| 2018/0214077 | A1 | 8/2018 | Dunki-Jacobs et al. |
| 2018/0271418 | A1 | 9/2018 | Hayter et al. |
| 2019/0236465 | A1 | 8/2019 | Vleugels |
| 2019/0246914 | A1 | 8/2019 | Constantin et al. |
| 2019/0252079 | A1 | 8/2019 | Constantin et al. |
| 2020/0129099 | A1 | 4/2020 | Mi et al. |
| 2020/0135320 | A1 | 4/2020 | Vleugels |
| 2020/0152312 | A1 | 5/2020 | Conner |

FOREIGN PATENT DOCUMENTS

| | | |
|---|---|---|
| WO | 2014115025 A1 | 7/2014 |
| WO | 2017027258 A1 | 2/2017 |

OTHER PUBLICATIONS

Gomez-Peralta et al., "A Novel Insulin Delivery Optimization and Tracking System," Diabetes Technology & Therapeutics, vol. 21, No. 4, Apr. 4, 2019, 6 pp.

U.S. Appl. No. 17/004,951, Naming Inventors: Weydt et al., filed Aug. 27, 2020.

U.S. Appl. No. 17/004,981, Naming Inventors: Weydt et al., filed Aug. 27, 2020.

International Search Report and the Written Opinion for corresponding International Application PCT/US2020/048461 dated Nov. 6, 2020, 14 Pages.

ly, to medical systems for therapy for diabetes.
GESTURE-BASED CONTROL OF DIABETES THERAPY This application claims the benefit of U.S. Provisional Application No. 62/893,717, filed Aug. 29, 2019, and U.S. Provisional Application No. 62/893,722, filed Aug. 29, 2019, the entire content of each of which is hereby incorporated by reference.

TECHNICAL FIELD

The disclosure relates to medical systems and, more particularly, to medical systems for therapy for diabetes.

BACKGROUND

A patient with diabetes receives insulin from a pump or injection device to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near mealtimes or other times where there may be a relatively fast change in glucose level, and may therefore serve as a short acting or rapid acting form of insulin dosage.

SUMMARY

Devices, systems, and techniques for gesture-based control of diabetes therapy are described. In various examples, gesture-based control of a patient device configured to deliver diabetes therapy to the patient protects that patient from being administered an improper and/or ineffective diabetes therapy. One or more processors (e.g., in a patient device such as an injection device for insulin delivery, a pump for insulin delivery, or another device; in a mobile or desktop computing device; and/or in one or more servers in a network cloud) may be configured to detect an impending delivery of the patient's diabetes therapy. In at least one example, the one or more processors may determine that an insulin injection is about to occur based upon the patient's (recent) activities including the patient's movements (e.g., hand movements). Various hardware/software components (e.g., accelerometers, optical sensors, gyroscopes, and/or the like) may capture and record the patient's activities as the user activity data, and by detecting the certain gestures in the user activity data, the one or more processors may predict an occurrence of an insulin injection.

Certain gestures are synonymous with insulin injections including gestures where the patient utilizes the injection device in some manner. If any of the patient's activities sufficiently resemble these gestures, the patient is most likely preparing to give him/herself an insulin injection. However, prior to the patient injecting the insulin, there may be benefits in ensuring that the correct amount of type of insulin is going to be injected. As described in more detail, the one or more processors may generate information indicative of amount of insulin and/or type of insulin dosage in the insulin injection that the patient is most likely preparing based on the gestures. The one or more processors may compare the information indicative of the amount or type of insulin dosage to a criteria of a proper insulin injection (e.g., such as amount of dosage, whether sufficient time has elapsed between insulin injections, whether a meal is consumed between insulin injections, whether the patient is using basal or bolus insulin based on time of day, and other such examples). If the criteria is not satisfied, the one or more processors may output an alert so that the patient does not inject him/herself or, more generally, perform some modification to correct an impropriety associated with the insulin injection or increase the efficacy of the insulin injection.

Although the above example is described with respect to a patient, the techniques are not so limited. The example techniques may be performed by a caregiver (e.g., at home or in hospital), and the example techniques may be for the caregiver. In general, the techniques may be applicable for a user, where a user is a generic term to refer to one or a combination of the patient and caregiver.

In one example, the disclosure describes a system having a wearable device configured to generate user activity data associated with an arm of a user, and one or more processors configured to: identify at least one gesture indicative of utilization of an injection device for preparation of an insulin injection based on the user activity data; based on the at least one identified gesture, generate information indicative of at least one of an amount or type of insulin dosage in the insulin injection by the injection device; compare the generated information to a criteria of a proper insulin injection; and output information indicative of whether the criteria is satisfied based on the comparison.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
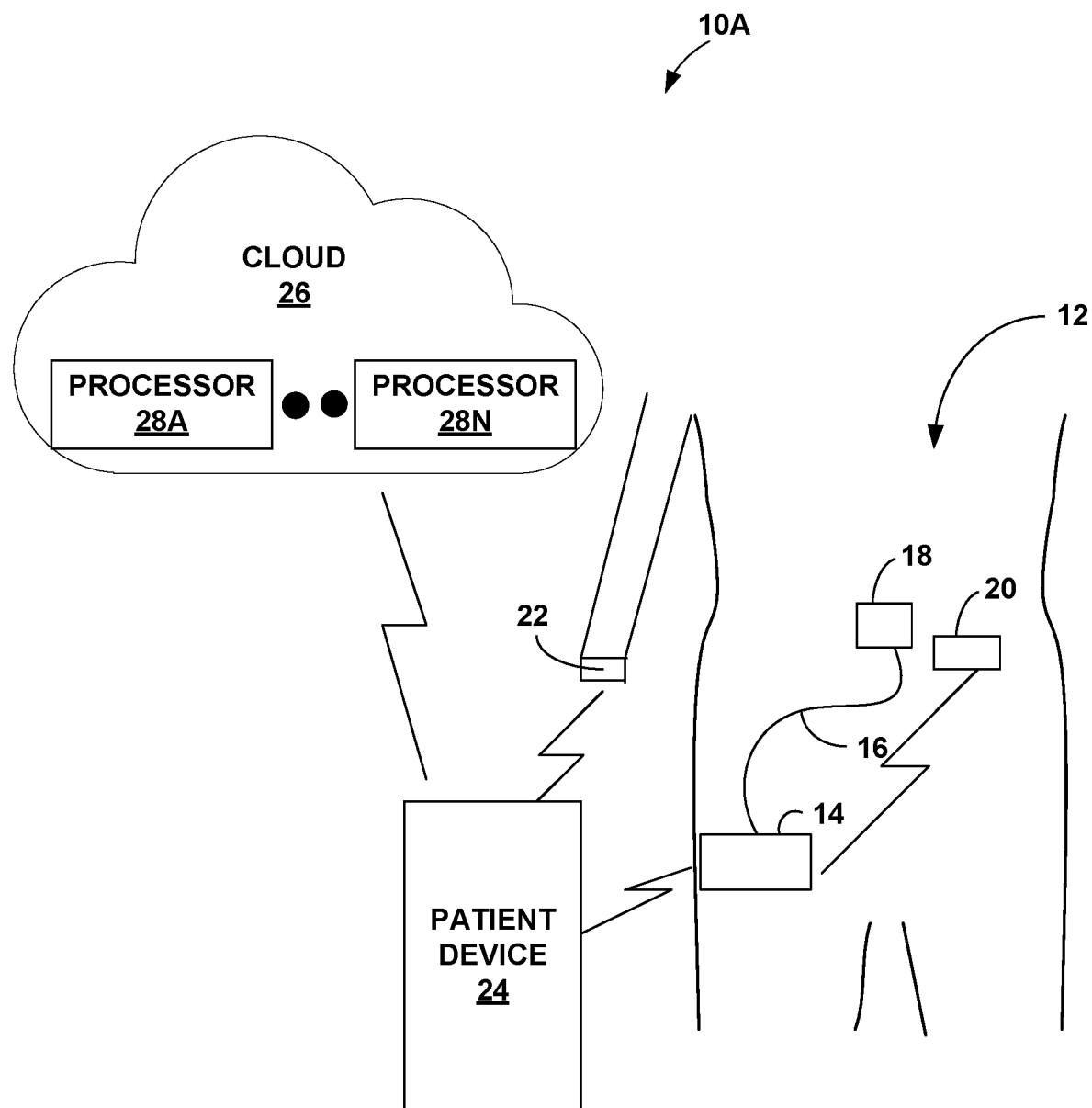
FIG. 1 is a block diagram illustrating an example system for delivering or guiding therapy dosage, in accordance with one or more examples described in this disclosure.

Devices, systems, and techniques for managing glucose level in a patient are described in this disclosure. Circumstances may exist where the administration of diabetes therapy unintentionally affects the patient's health, for example, causing the patient to receive an ineffective or incorrect amount or type of insulin. Because some patients manage their own diabetes therapy (e.g., via an injection device for delivering a dose of insulin), these patients have ample opportunities to impact (e.g., offset) their glucose levels. Given that most people have busy lives, the patient may become preoccupied and simply forget to take their insulin at a recommended time. Sometimes, several minor disruptions throughout a given day interrupt the patient's recommended injection schedule. Even if the patient remembers a scheduled insulin injection, the patient may still forget the proper dosage amount or a type of insulin to administer. The patient may forget which settings on the injection device to apply in order to prepare an injection with the proper amount and/or type of insulin. Even if the patient employs a caregiver to assist his/herself with insulin injections or perform the insulin injections, the caregiver also is capable of making an error in administering diabetes therapy.

It should be noted that a variety of injection devices are described herein as being applicable to the devices, systems, and techniques of the disclosure. Some injection devices may be manual injection devices (e.g., a syringe) while other injection devices (e.g., "smart" injection devices) may be equipped with processing circuitry and/or sensing technology. In some examples, "smart" caps may be configured to attach to syringes or go over the insulin pens. It should be noted that a cloud service (e.g., running on servers of a network cloud) may provide a number of benefits to the patient including remote medical services, managed medical care, and/or access to a network of medical professionals. The cloud service may operate with a number of devices (e.g., a patient device, a caregiver device, the injection device, and/or any other compatible computing device) to provide a remote monitoring system (e.g., MEDTRONIC® CARELINK™) through which the user may be notified of pending improper diabetes therapy (e.g., improper insulin injections), general and diabetes-specific health issues including those caused by improper diabetes therapy, and other critical transmissions via alerts (e.g., CAREALERT™ notifications).

In this disclosure, the devices, systems, and techniques for managing the patient's glucose level include devices, systems, and techniques for gesture-based control of diabetes therapy. Gesture-based control, as described herein, involves protecting the patient from the consequences of receiving incorrect and/or ineffective diabetes therapy, for example, in form of improper insulin injections. By detecting one or more gestures that indicate an insulin injection is about to occur or is occurring, the devices, systems, and techniques for gesture-based control may determine whether some aspect of that injection is improper with enough time to notify a user (e.g., the patient or a caregiver) of one or more improprieties in the patient's pending injection (e.g., in the injective device's settings) before the user completes the insulin injection. In this manner, the user is afforded an opportunity to stop the insulin injection and/or modify the device's settings to remove at least one impropriety.

To illustrate by way of example, if the patient forgets a recent insulin injection and attempts an insulin injection at an improper time and/or with an insufficient interval between injections, the devices, systems, and techniques described herein may output an alert indicative of the improper insulin injection. As an alternative, if the patient forgets the injection schedule and is about to miss a scheduled injection, the devices, systems, and techniques described herein may output an alert indicative of the missed injection. One or more processors (e.g., in a mobile computing device known as the patient device, in a network cloud server providing the cloud service, or in the injection device itself) may generate the alert to include any content type (e.g., video, audio, text) and output that alert through any mechanism (e.g., an electronic display, tactile responses (e.g., vibrations), and/or the like).

The one or more processors may generate the alert to notify any user of the injection device, including the patient via the patient device or the injection device or the patient's home caregiver via a caregiver device. The caregiver may be a home caregiver (e.g., a family member or friend, a nurse, and/or the like), a medical professional (e.g., a doctor or a nurse) in a medical facility (e.g., a hospital), or another professional in charge of the patient's health. The one or more processors may communicate the alert from a handheld patient device to the injection device, to the network cloud server, and/or to the caregiver device. As an alternative, the one or more processors may communicate the alert from the network cloud server to the injection device, to the patient device, and/or to the caregiver device. In some examples where processing circuitry within the injection device executes logic (e.g., processor-executable instructions or code) for gesture-based control, the injection device may generate the alert for display on an electronic display of the injection device itself and/or communicate, to the patient device, a network cloud server, a caregiver device, and/or another external device, the alert to notify the patient, the cloud service, and/or the caregiver.

Even if the user prepares the insulin injection at a proper time, the user is capable of preparing the injection with an ineffective dosage amount and/or type of insulin. Some example patient gestures correspond to setting the dosage amount and/or type on the injection device and by detecting these gestures, it is possible to ascertain actual dosage amounts and/or types. If, for instance, the injection device has a dial for setting the dosage amount, the patient may make a gesture moving the dial a number of clicks where each click increases the insulin amount being loaded into a chamber of the injection device. This gesture may be detected by one or more sensors in a wearable device attached to the user's body, an activity monitor, and/or in the injection device itself. If the detected dosage amount fails to match the recommended dosage amount but is within a certain range, the detected dosage amount may be considered ineffective while detected dosage amounts without the certain range may be considered lethal. In some examples, the patient may not face severe consequences from being given an ineffective dosage of insulin in contrast with a lethal dosage. In response to a predication of an imminent injection of an ineffective or lethal dosage amount, the devices, systems, and techniques for gesture-based control may notify the patient by displaying, on an electronic display, an alert configured to present various types of content (e.g., text, graphical content, video content, and/or the like) as well as tactile and audible alerts. In some examples, the devices, systems, and techniques for gesture-based control may display data informing the patient as to which one or more device settings to modify in order to correct the ineffective dosage amount.

Depending on which injection device a given diabetes patient utilizes, the injection device may implement one or more technologies to detect insulin injections (during preparation or after occurrence), record various information for each injection, and/or notify the patient (e.g., via a textual warning or audible alert) if there is a problem (e.g., impropriety) with any particular injection. Some manufacturers instrument their injection devices with one or more sensors to perform the detection, recordation, and notification as mentioned above; however, some patients use injection devices that are equipped with either a minimal level of sensing technology or no sensing technology whatsoever, leaving the patient or the patient's caregiver the responsibility of properly administering the patient's diabetes therapy. An external device (e.g., wearable device, the patient device, or another mobile computing device) having sensing technology may provide sensor data for identifying one or more gestures indicative of the insulin injection. Some of the injection devices described herein (e.g., insulin pens or syringes) may be retrofit with sensing technology (e.g., in a smart insulin pen cap).

Injective devices other than those described herein are unable to provide gesture-control and protection of patient health. These devices are limited in a number of areas including knowledge of the patient's proper diabetes therapy in terms of dosage amount, insulin type (e.g., bolus insulin), dosage schedule, and other parameters. Even if some injection devices are able to detect dosage amount or insulin type through various means, none operate with a wearable or another external device to identify dosage amount or insulin type.

The devices, systems, and techniques described herein are configured to mitigate or eliminate altogether the injection device's limitations as mentioned above. In some examples, one or more sensors in one device may provide one or more processors (e.g., processing circuitry) in the same device or a different device with data describing various user activities (e.g., patient activities or caregiver activities) including movement(s) of the user's hand and/or arm and/or pose(s) (e.g., positioning and/or orientation) of the user's hand while holding the injection device. Some example sensors are communicably coupled to the one or more processors while some sensors are directed coupled to the one or more processors.

Hence, the one or more processors may receive user activity data from one or more internal sensors, one or more sensors in the injection device, and/or one or more sensors in another device, such as a wearable device attached to a body part of the patient. In one example, a wearable device (known as a smart watch) may be attached to one of the patient's hands and instrumented with inertial measurement units (e.g., one or more accelerometers) capable of capturing user activities (e.g., user movements and/or user poses) including gestures synonymous with an insulin injection. If the injection device is configured with little or no sensing technology, an accelerometer in the wearable device or another external device may provide the user activity data enabling the prediction of an insulin injection and/or the injection device data enabling confirmation (or rejection) of the prediction of an insulin injection.

In some examples, the devices, systems, and techniques described herein may leverage data provided by the injection device to confirm a prediction of an insulin injection based upon an identification of one or more gestures by the user. To illustrate by way of example, after identifying a gesture to set the dosage amount and type on the injection device, a sensor may sense that a cartridge has been loaded into the injection device in preparation for administering the insulin injection, confirming that gesture identification. The user may provide input data confirming preparation of the insulin injection (e.g., a patient confirmation). Confirmation may be achieved through injective device data provided by other devices such as a device having a sensor to detect an insulin dose in a syringe barrel. Sensor data may be used to predict that the insulin injection has been prepared as well as predict that the insulin injection occurred (e.g., recently). A sensor for reading insulin levels in the injection device may measure first and second insulin levels and determine that an intervening insulin injection lowered the insulin level from the first to the second level. One benefit of confirmation is that the user activity data supporting the prediction may be provided by an unreliable external sensor and/or include inaccurate or incorrect sensor data; in effect, the confirmation serves to mitigate the unreliability of the external sensor and the inaccuracy or incorrectness of the external sensor data. As another benefit of the confirmation, the one or more processors may operate with injection devices that do not have any inertial measurement units or other sensors. In effect, confirmation via the injection device or the injection device data allows the one or more processors to rely on the wearable device for the user activity data without having to implement an internal sensor or rely on the injection device's sensor(s).

FIG. 1 is a block diagram illustrating an example system for delivering or guiding therapy dosage, in accordance with one or more examples described in this disclosure. FIG. 1 illustrates system 10A that includes patient 12, insulin pump 14, tubing 16, infusion set 18, sensor 20, which may be a glucose sensor, wearable device 22, patient device 24, and cloud 26. Cloud 26 represents a local, wide area or global computing network including one or more processors 28A-28N ("one or more processors 28"). In some examples, the various components may determine changes to therapy based on determination of glucose level for sensor 20, and therefore system 10A may be referred to as a continuous glucose monitoring (CGM) system 10A.

Patient 12 may be diabetic (e.g., Type 1 diabetic or Type 2 diabetic), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Sensor 20 may also be coupled to patient 12 to measure glucose level in patient 12. Insulin pump 14, tubing 16, infusion set 18, and sensor 20 may together form an insulin pump system. One example of the insulin pump system is the MINIMED™ 670G INSULIN PUMP SYSTEM by Medtronic, Inc. However, other examples of insulin pump systems may be used and the example techniques should not be considered limited to the MINIMED™ 670G INSULIN PUMP SYSTEM. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or sensor 20 may be contained in the same housing.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Sensor 20 may include a cannula that is inserted under the skin of patient 12, such as near the stomach of patient 12 or in the arm of patient 12 (e.g., subcutaneous connection). Sensor 20 may be configured to measure the interstitial glucose level, which is the glucose found in the fluid between the cells of patient 12. Sensor 20 may be configured to continuously or periodically sample the glucose level and rate of change of the glucose level over time.

In one or more examples, insulin pump 14 and sensor 20, and the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from sensor 20, and in response may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

For example, insulin pump 14 and sensor 20 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, sensor 20 may sample glucose level and rate of change in glucose level over time. Sensor 20 may output the glucose level to insulin pump 14 (e.g., through a wireless link connection like Bluetooth or BLE). Insulin pump 14 may compare the glucose level to a target glucose level (e.g., as set by patient 12 or clinician), and adjust the insulin dosage based on the comparison. In some examples, sensor 20 may also output a predicted glucose level (e.g., where glucose level is expected to be in the next 30 minutes), and insulin pump 14 may adjust insulin delivery based on the predicted glucose level.

As described above, patient 12 or a clinician may set the target glucose level on insulin pump 14. There may be various ways in which patient 12 or the clinician may set the target glucose level on insulin pump 14. As one example, patient 12 or the clinician may utilize patient device 24 to communicate with insulin pump 14. Examples of patient device 24 include mobile devices, such as smartphones or tablet computers, laptop computers, and the like. In some examples, patient device 24 may be a special programmer or controller for insulin pump 14. Although FIG. 1 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may be one or more patient devices.

Patient device 24 may also be configured to interface with sensor 20. As one example, patient device 24 may receive information from sensor 20 through insulin pump 14, where insulin pump 14 relays the information between patient device 24 and sensor 20. As another example, patient device 24 may receive information (e.g., glucose level or rate of change of glucose level) directly from sensor 20 (e.g., through a wireless link).

In one or more examples, patient device 24 may display a user interface with which patient 12 or the clinician may control insulin pump 14. For example, patient device 24 may display a screen that allows patient 12 or the clinician to enter the target glucose level. As another example, patient device 24 may display a screen that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through patient device 24 is one example, and should not be considered limiting. For example, insulin pump 14 may include a user interface (e.g., pushbuttons) that allow patient 12 or the clinician to set the various glucose levels of insulin pump 14. Also, in some examples, insulin pump 14 itself, or in addition to patient device 24, may be configured to output notifications to patient 12. For instance, if the glucose level is too high or too low, insulin pump 14 may output an audible or haptic output. As another example, if the battery is low, then insulin pump 14 may output a low battery indication on a display of insulin pump 14.

The above describes examples ways in which insulin pump 14 may deliver insulin to patient 12 based on the current glucose levels (e.g., as measured by sensor 20). In some cases, there may be therapeutic gains by proactively delivering insulin to patient 12, rather than reacting to when glucose levels become too high or too low.

The glucose level in patient 12 may increase due to particular user actions. As one example, the glucose level in patient 12 may increase due to patient 12 engaging in an activity like eating or exercising. In some examples, there may be therapeutic gains if it is possible to determine that patient 12 is engaging in the activity, and delivering insulin based on the determination that patient 12 is engaging in the activity.

For example, patient 12 may forget to cause insulin pump 14 to deliver insulin after eating, resulting an insulin shortfall. Alternatively, patient 12 may cause insulin pump 14 to deliver insulin after eating but may have forgotten that patient 12 previously caused insulin pump 14 to deliver insulin for the same meal event, resulting in an excessive insulin dosage. Also, in examples where sensor 20 is utilized, insulin pump 14 may not take any action until after the glucose level is greater than a target level. By proactively determining that patient 12 is engaging in an activity, insulin pump 14 may be able to deliver insulin in such a manner that the glucose level does not rise above the target level or rises only slightly above the target level (i.e., rises by less than what the glucose level would have risen if insulin were not delivered proactively). In some cases, by proactively determining that patient 12 is engaging in an activity and delivering insulin accordingly, the glucose level of patient 12 may increase more slowly.

Although the above describes proactive determination of patient 12 eating and delivering insulin accordingly, the example techniques are not so limited. The example techniques may be utilized for proactively determining an activity that patient 12 is undertaking (e.g., eating, exercising, sleeping, driving, etc.). Insulin pump 14 may then deliver insulin based on the determination of the type of activity patient 12 is undertaking.

As illustrated in FIG. 1, patient 12 may wear wearable device 22. Examples of wearable device 22 include a smartwatch or a fitness tracker, either of which may, in some examples, be configured to be worn on a patient's wrist or arm. In one or more examples, wearable device 22 includes inertial measurement unit, such as a six-axis inertial measurement unit. The six-axis inertial measurement unit may couple a 3-axis accelerometer with a 3-axis gyroscope. Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions). Wearable device 22 may be configured to determine one or more posture characteristics of patient 12 including values relating to position and/or an orientation.

Patient 12 may wear wearable device 22 on his or her wrist. However, the example techniques are not so limited. Patient 12 may wear wearable device 22 on a finger, forearm, or bicep. In general, patient 12 may wear wearable device 22 anywhere that can be used to determine gestures indicative of eating, such as movement characteristics of the arm.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency at which patient 12 moves his or her arm or a pattern at which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect movements of the arm of patient 12 (e.g., one or more movement characteristics), and the movement characteristics may be utilized to determine an activity undertaken by patient 12. For instance, the movement characteristics detected by wearable device 22 may indicate whether patient 12 is exercising, driving, sleeping, etc. As another example, wearable device 22 may indicate posture of patient 12, which may align with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, injecting insulin, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to patient device 24, and patient device 24 may be configured to determine the activity patient 12 is undertaking.

Wearable device 22 and/or patient device 24 may be programmed with information that wearable device 22 and/or patient device 24 utilize to determine the particular activity patient 12 is undertaking. For example, patient 12 may undertake various activities throughout the day where the movement characteristics of the arm of patient 12 may be similar to the movement characteristics of the arm of patient 12 for a particular activity, but patient 12 is not undertaking that activity. As one example, patient 12 yawning and cupping his or her mouth may have a similar movement as patient 12 eating. Patient 12 picking up groceries may have similar movement as patient 12 exercising. Also, in some examples, patient 12 may be undertaking a particular activity, but wearable device 22 and/or patient device 24 may fail to determine that patient 12 is undertaking the particular activity.

Accordingly, in one or more examples, wearable device 22 and/or patient device 24 may "learn" to determine whether patient 12 is undertaking a particular activity. However, the computing resources of wearable device 22 and patient device 24 may be insufficient to performing the learning needed to determine whether patient 12 is undertaking a particular activity. It may be possible for the computing resources of wearable device 26 and patient device 24 to be sufficient to perform the learning, but for ease of description only, the following is described with respect to one or more processors 28 in cloud 26.

As illustrated in FIG. 1, system 10A includes cloud 26 that includes one or more processors 28. For example, cloud 26 includes a plurality of network devices (e.g., servers), and the plurality of devices each include one or more processors. One or more processors 28 may be processors of the plurality of network devices, and may be located within a single one of the network devices, or may be distributed across two or more of the network devices. Cloud 26 represents a cloud infrastructure that supports one or more processors 28 on which applications or operations requested by one or more users run. For example, cloud 26 provides cloud computing for using one or more processors 28, to store, manage, and process data on the network devices, rather than by personal device 24 or wearable device 22. One or more processors 28 may share data or resources for performing computations, and may be part of computing servers, web servers, database servers, and the like. One or more processors 28 may be in network devices (e.g., servers) within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

In some examples, one or more processors 28 may be configured to determine patterns from gesture movements (e.g., as one or more movement characteristics determined by wearable device 22), and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). Cloud 26 and patient device 24 may communicate via Wi-Fi or through a carrier network.

For example, as described above, in some examples, wearable device 22 and/or patient device 24 may be configured to determine that patient 12 is undertaking an activity. However, in some examples, patient device 24 may output information indicative of the movement characteristics of movement of the arm of patient 12 to cloud 26, and possibly with other contextual information like location or time of day. One or more processors 28 of cloud 26 may then determine the activity patient 12 is undertaking. Insulin pump 14 may then deliver insulin based on the determined activity of patient 12.

One example way in which one or more processors 28 may be configured to determine that patient 12 is undertaking an activity and determine therapy to deliver is described in U.S. Patent Publication No. 2020/0135320 A1. In general, one or more processors 28 may first go through an initial "learning" phase, in which one or more processors 28 receive information to determine behavior patterns of patient 12. Some of this information may be provided by patient 12. For example, patient 12 may be prompted or may himself/herself enter information into patient device 24 indicating that patient 12 is undertaking a particular activity, the length of the activity, and other such information that one or more processors 28 can utilize to predict behavior of patient 12. After the initial learning phase, one or more processors 28 may still update the behavior patterns based on more recent received information, but require fewer to no information from patient 12.

In the initial learning phase, patient 12 may provide information about the dominant hand of patient 12 (e.g., right or left-handed) and where patient 12 wears wearable device 22 (e.g., around the wrist of right hand or left hand). Patient 12 may be instructed to wear wearable device 22 on the wrist of the hand patient 12 uses to eat. Patient 12 may also provide information about the orientation of wearable device 22 (e.g., face of wearable device 22 is on the top of the wrist or bottom of the wrist).

In the initial learning phase, patient 12 may enter, proactively or in response to prompt/query, information (e.g., through patient device 24) indicating that patient 12 is engaging in an activity. During this time, wearable device 22 may continuously determine the one or more movement and/or posture characteristics (e.g., gestures) of patient 12, and output such information to patient device 24 that relays the information to one or more processors 28. One or more processors 28 may store information of the one or more movement characteristics of movement of the arm of patient 12 during the activity to later determine whether patient 12 is engaging in that activity (e.g., whether the received information of the manner and frequency of movement of the arm of patient 12 aligns with the stored information of the manner and frequency of movement of the arm of patient 12 when patient 12 was known to be engaging in that activity).

The above describes arm movement as a factor in determining whether patient 12 is engaging in an activity. However, there may be various other factors that can be used separately or in combination with arm movement to determine whether patient 12 is engaging in an activity. As one example, patient 12 may engage in the activity at regular time interval. As another example, patient 12 may engage in the activity at certain locations. In the initial learning phase, when patient 12 enters that he or she is engaging in the activity (e.g., through patient device 24), patient device 24 may output information about the time of day and the location of patient 12. For example, patient device 24 may be equipped with a positioning device, such as global positioning system (GPS) unit, and patient device 24 may output location information determined by the GPS unit. There may be other ways to determine location such as based on Wi-Fi connection and/or access to 4G/5G LTE, or some other form of access, such as based on telecom database tracking device location of patient device 24. Time of day and location are two examples of contextual information that can be used to determine whether patient 12 is engaging in the activity.

However, there may be other examples of contextual information for patient 12 such as sleep pattern, body temperature, stress level (e.g., based on pulse and respiration), heart rate, etc. In general, there may be various biometric sensors (e.g., to measure temperature, pulse/heart rate, breathing rate, etc.), which may be part of wearable device 22 or may be separate sensors. In some examples, the biometric sensors may be part of sensor 20.

The contextual information for patient 12 may include conditional information. For example, patient 12 may eat every 3 hours, but the exact times of when patient 12 eats may be different. In some examples, the conditional information may be a determination of whether patient 12 has eaten and if a certain amount of time (e.g., 3 hours) has passed since patient 12 ate. In general, any information that establishes a pattern of behavior may be utilized to determine whether patient 12 is engaging in a particular activity.

One or more processors 28 may utilize artificial intelligence, such as machine-learning or other data analytics techniques, based on the information determined by and/or collected by wearable device 22 and patient device 24 to determine whether patient 12 is engaging in the activity. As one example, during the initial learning phase, one or more processors 28 may utilize neural network techniques. For example, one or more processors 28 may receive training data from patient 12 that is used to train a classifier module executing on one or more processors 28. As described above, one or more processors 28 may receive the training data based on patient confirmation when patient device 24 and/or wearable device 22 determine, based on manner and frequency of movement of the arm of patient 12, that patient 12 is engaging in the activity (e.g., a gesture that aligns with movement of arm for eating). One or more processors 28 may generate and store a labeled data record that includes the features related to the movement, along with other contextual features, such as time of day or location. One or more processors 28 may train the classifier on a labeled dataset that includes multiple labeled data records, and one or more processors 28 may use the trained classifier model to more accurately detect the start of a food intake event.

Other examples that may be used for neural networks include behavior patterns. For example, patient 12 may only eat a particular food after exercising, and always eats that particular food after exercising. Patient 12 may eat at a particular time and/or place. Although described with respect to eating, there may be various conditions that together indicate a pattern in behavior of patient 12 for different activities.

As another example, one or more processors 28 may utilize k-means clustering techniques to determine whether patient 12 is engaging in an activity. For example, during the initial learning phase one or more processors 28 may receive different types of contextual information and form clusters, where each cluster represents a behavior of patient 12 (e.g., eating, sleeping, walking, exercising, etc.). For example, patient 12 may enter information (e.g., into patient device 24) indicating that he or she is walking. One or more processors 28 may utilize all the contextual information received when patient 12 is walking to form a first cluster associated with walking. Patient 12 may enter information (e.g., into patient device 24) indicating that he or she is eating. One or more processors 28 may utilize all the contextual information received when patient 12 is eating to form a second cluster associated with eating, and so on. Then, based on received contextual information, one or more processors 28 may determine which cluster aligns with the contextual information, and determine the activity patient 12 is undertaking. As described in more detail, the type of activity, and a prediction of when the activity will occur, may be utilized to determine when to delivery insulin therapy. There may be other examples of machine learning, and the example techniques are limited to any particular machine learning technique.

There may be various other ways in which one or more processors 28 may determine the activity patient 12 is undertaking. This disclosure provides some example techniques for determining the activity patient 12 is undertaking, but the example techniques should not be considered limiting.

During the initial learning phase, patient 12 may also enter information about the activity that patient 12 is undertaking. For example, with eating, patient 12 may enter information indicating what patient 12 is eating and/or how many carbohydrates there are in the food that patient 12 is eating. As one example, at 9:00 every morning, patient 12 may enter that he or she is having a bagel or enter that the patient 12 is consuming 48 grams of carbohydrates.

In some examples, one or more processors 28 may be configured to determine an amount of insulin (e.g., therapy dosage of bolus insulin) to deliver to patient 12. As one example, memory accessible by one or more processors 28 may store patient parameters of patient 12 (e.g., weight, height, etc.). The memory may also store a look-up table that indicates an amount of bolus insulin that is to be delivered for different patient parameters and different types of foods. One or more processors 28 may access the memory and based on the type of food patient 12 is eating and patient parameters may determine the amount of bolus insulin that patient 12 is to receive.

As another example, one or more processors 28 may be configured to utilize a "digital twin" of patient 12 to determine an amount of bolus insulin patient 12 is to receive. A digital twin may be a digital replica or model of patient 12. The digital twin may be software executing on one or more processors 28. The digital twin may receive, as input, information about what patient 12 ate. Because the digital twin is a digital replica of patient 12, the output from the digital twin may be information about what the glucose level of patient 12 may be after eating, as well as a recommendation of how much bolus insulin to deliver to patient 12 to control the increase the glucose level.

For example, the digital twin may indicate what the correct dose should have been for a meal that patient 12 ate in the past. In one or more examples, patient 12 may enter information indicative of food patient 12 ate and one or more processors 28 may receive information about glucose levels. Utilizing information indicative of food that patient 12 ate and glucose levels, one or more processors 28 may utilize the digital twin to determine what the insulin dose should have been (e.g., based on how the digital twin models how the food will affect the patient's glucose level). Then, at a subsequent time when patient 12 is predicted to eat the same meal, one or more processors 28 may determine what the insulin dose should be based on insulin dose amount that the digital twin had previously determined.

Accordingly, in one or more examples, one or more processors 28 may utilize information about the movement characteristics of movement of arm, eating pace, quantity of food consumption, food content, etc., while also tracking posture characteristics and other contextual information. Examples of the contextual information include location information, time of day, wake up time, amount of time since last eaten, calendar event, information about person patient 12 may be meeting, etc. One or more processors 28 may identify patterns and correlations between all these various factors to determine an activity patient 12 undertaking, like eating, walking, sleeping, driving, etc.

After the initial learning phase, one or more processors 28 may automatically, and with minimal input from patient 12, determine that patient 12 is undertaking a particular activity, and determine an amount of bolus insulin to deliver based on the determination. One or more processors 28 may output the recommendation of the amount of bolus insulin to deliver to patient device 24. Patient device 24, may then in turn, control insulin pump 14 to deliver the determined amount of insulin. As one example, patient device 24 may output to insulin pump 14 the amount of bolus insulin to deliver with or without user confirmation. As another example, patient device 24 may output a target glucose level, and insulin pump 14 may deliver the insulin to achieve the target glucose level. In some examples, it may be possible for one or more processors 28 to output to patient device 24 information indicative of the target glucose level, and patient device 24 may output that information to insulin pump 14. All of these examples may be considered as examples of one or more processors 28 determining an amount of insulin to deliver to patient 12.

The above describes example ways in which to determine if patient 12 is undertaking an activity, determining an amount of insulin to deliver, and causing the amount of insulin to be delivered. The example techniques may require little to no intervention from patient 12. In this manner, there is an increase in likelihood that patient 12 will receive the correct amount of dosage of insulin at the right time, and decrease in likelihood of human error causing issues (e.g., patient 12 forgetting to log meals, forgetting to take insulin, or taking insulin but forgetting to have taken insulin).

While the above example techniques may be beneficial in patient 12 receiving insulin at the right time, this disclosure describes example techniques to further proactively control delivery of insulin to patient 12. For example, the above describes examples where patient 12 is wearing insulin pump 14. However, there may be times where patient 12 could not wear insulin pump 14, and needs to manually inject insulin. There may also be times where patient 12 does not have insulin dosage for the reservoir of insulin pump 14. The above techniques described for determining amounts of insulin to deliver and when to deliver the insulin may also be useful in situations where insulin pump 14 is not available. For example, as described in more detail below with respect to FIGS. 2 and 3, rather than insulin pump 14, patient 12 may utilize an injection device, like insulin pen, syringe, etc. In utilizing the injection device, even when notified to inject himself/herself, patient 12 may miss the dosage or put in the incorrect amount of insulin.

This disclosure describes examples of utilizing activity data, to determine gesture information indicative of patient 12 (or possibly a caregiver) preparing an insulin injection or actually injecting insulin. The example techniques may determine whether a criteria of proper insulin injection is satisfied or not to alert patient 12 in case the criteria is not satisfied.

In particular, this disclosure describes example techniques to control deliverance of therapy to a diabetes patient where the therapy involves timely injections of an effective amount of a correct type of insulin. To effectuate these techniques, one or more processors 28 may first predict that an insulin injection is about to occur in response to an identification of one or more gestures indicative of the insulin injection and then, determine whether the predicted insulin injection is proper or improper for patient 12 by comparing parameter data and other information for the insulin injection with established criteria of a proper insulin injection. The parameter data and other information may be indicative of an amount or a type of insulin dosage.

The established criteria may be communicated by network servers of a cloud service in control over injection device 30, patient device 24, or any other compatible device and/or entered, as input, by medical professionals using injection device 30, patient device 24, or any other compatible device. The established criteria may include recommended and/or effective values/classifications for various insulin injection parameters including insulin dosage amount, insulin type, and/or injection schedule (or alternatively, a time interval between injections). Examples of the criteria of the proper insulin injection include one or more of a number of clicks (or rotation(s) of an insulin pen dial) used to set the insulin dosage amount, an amount of time that elapsed between insulin injections, whether the user consumed a meal between insulin injections, whether the patient is injecting with a basal insulin based on time of day, or whether the patient is injecting with a bolus insulin based on time of day. Some techniques employ additional parameters and/or different parameters including an injection site/area, trajectory, and/or the like. If the parameter data for the insulin injection does not satisfy the criteria of a proper insulin injection, one or more processors 28 may output, for display on an electronic display, an alert notifying patient 12 that an improper insulin injection is to occur.

In some examples, one or more processors 28 may build a data model configured to distinguish between user activities, such as between a user activity of injecting insulin and a user activity of eating. In the initial learning phase, by training the data model with user activity data and injection device data, one or more processors 28 may generate the data model to identify any user activity mentioned in in the present disclosure. In some examples, one or more processors 28 may employ the trained data model to predict whether or not patient 12 ate any food based upon features derived from movement characteristics, posture characteristics, and other contextual information as features. In some examples, one or more processors 28 may employ the trained data model to determine whether patient 12 is predicted to use basal or bolus insulin.

Figure 2:
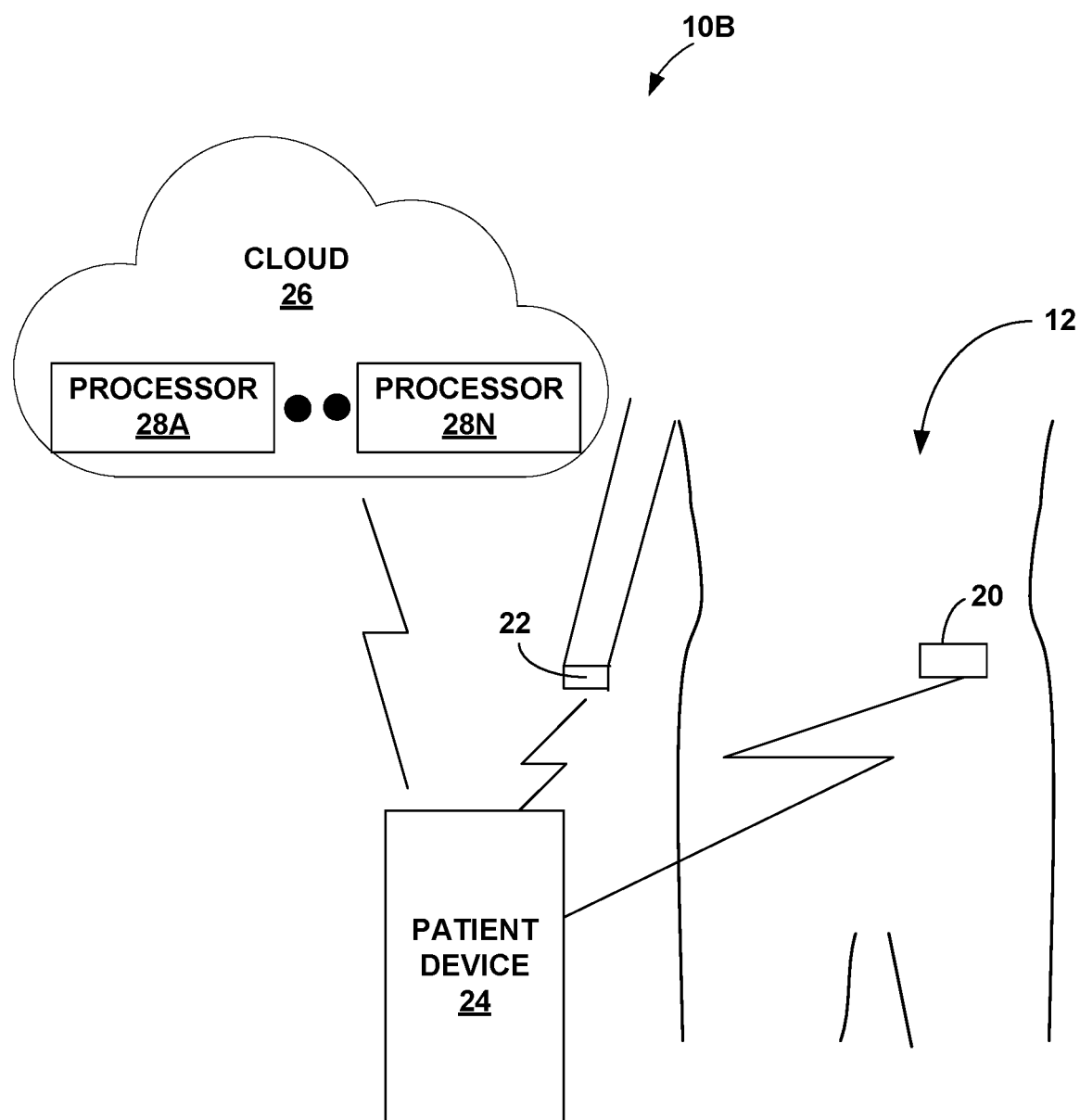
FIG. 2 is a block diagram illustrating another example system for delivering or guiding therapy dosage, in accordance with one or more examples described in this disclosure.

FIG. 2 is a block diagram illustrating another example system for delivering or guiding therapy dosage, in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or syringe) to deliver insulin. For example, rather than insulin pump 14 automatically delivering insulin, patient 12 (or possible a caretaker of patient 12) may fill a syringe with insulin or set the dosage amount in an insulin pen and inject himself or herself.

System 10B, implementing the example techniques and devices described herein, protects patient 12 from injecting himself or herself at an improper time and/or with an improper (e.g., ineffective) dosage amount or type of insulin. To effectuate this protection, one or more processors 28 may compare information indicative of a current time or a set amount and/or type of a pending insulin injection to criteria of a proper insulin injection and if that comparison indicates non-satisfaction with at least one criterion, employ a technique to halt (or delay) the pending insulin injection and/or modify the set amount and/or type of insulin. As a result, one or more processors 28 prevent the patient from being injected with an incorrect amount and/or type of insulin and/or at an incorrect time. Consequences from improper insulin injections may range from minor discomfort to major declination in patient health. For example, if not enough time elapsed between a previous insulin injection and a current insulin injection, there is a possibility that the patient simply forgot about the previous insulin injection. If patient 12 did not eat any food between injections, the patient may end up with low glucose level.

In system 10B, one or more processors 28 capture sensor data provided by one or more inertial measurement units (e.g., in wearable device 22) and indicative of various user activities (i.e., user activity data). At least a portion of this user activity data captures characteristics of user movements and/or user posture while holding any injection device; examples of such characteristics include user hand movements, user hand pose (e.g., positioning/orientation), and/or the like). The user may be patient 12, a caregiver of patient 12, or any other provider of an insulin injection to patient 12. As described herein, the captured user activity data may be inclusive of all user activities and not specific to user activities involving the insulin pen or the syringe or another manual injection device. For at least this reason, the user activity data may include gestures that could be mistaken for a gesture indicative of an insulin injection. For example, refilling the syringe and preparing/administering an insulin injection with the syringe may involve same or similar gesture(s) and any user activity indicating such a refill event constitutes indicia of non-occurrence of the insulin injection.

In addition, the user activity data may include inaccuracies, for example, resulting from limitations in one or more inertial measurement units. When an inertial measurement unit in wearable device 22 generates sensor data (e.g., accelerometer data), that data is often raw or unrefined. The user activity data may be a higher-level abstraction of the sensor data generated by the one or more sensors. While the accelerometer data may describe two positions in three-dimensional space and a movement between these positions, the captured user activity data may describe the same movement in a different space or a combination of two or more movements between positions in three-dimensional space. The user activity data may describe a gesture or a portion thereof as a cohesive sequence of patient movements.

For any type of injection device, one or more processors 28, implementing the example techniques, may build and train a data model until that data model is able to distinguish between gestures indicative of an insulin injection from other patient gestures. To illustrate, an example data model may use accelerometer data to define movement characteristics (e.g., vibrations, accelerations, and/or the like), posture characteristics (e.g., positioning and orientation), and other characteristics for a gesture of holding the injection device at a particular position and/or a particular orientation for administrating diabetes therapy. The particular position and/or the particular orientation may be pre-determined (e.g., by device manufacturer) and/or learned over time. The particular position and/or the particular orientation may be recommended by the patient caregiver and/or determined to be effective (e.g., most effective) for diabetes therapy by a medical professional. Another detectable gesture includes setting an insulin dosage amount for the manual injection device (e.g., by pumping insulin into syringe barrel, turning a dial on an insulin pen, and/or the like). Other detectable user activity gestures corresponding to a manual insulin injection include a gesture moving the injection device closer to the patient's body, a gesture returning the manual injection device to a safe location (e.g., in medical waste disposal unit), a gesture removing air bubbles from the manual injection device (e.g., syringe barrel), a gesture refilling the manual injection device with a subsequent insulin dose (e.g., a refill event), among others.

A given data model for gesture detection may define one or more detectable insulin injection instances as any combination of the above-mentioned gestures. Some gestures rank higher than others and are given priority. Some gestures are cotemporaneous, frequently occurring when insulin injections also occur. Some gestures correlate to a possible impact on the effectiveness of the diabetes therapy being administered to patient 12, such as the above-mentioned gesture to remove air bubbles from the manual injection device. Although some example techniques and systems employ multiple sensors 20, composite gestures for delivering an insulin dose through the manual injection device are detectable using data provided by a single sensor 20 known as an inertial measurement unit (e.g., accelerometer and gyroscope). Accomplishing gesture detection for insulin injections as described herein benefits patient 12 with immediate results when any user activity occurs or is about to occur. Patient 12 is not burdened with complicated setup and/or operational tasks. In some examples, patient 12 does not perform any activity other than corresponding user activities for injecting an insulin dose while one or more processors 28 (and/or hardware/software component(s) of patient device 24) predict that the insulin injection is about to occur.

Prior to patient 12 or a caregiver of patient 12 injecting the insulin, there may be benefits in ensuring that the appropriate amount and/or correct type of insulin is going to be injected. One or more processors 28 may generate information indicative of amount of insulin and/or type of insulin dosage in the insulin injection that patient 12 or the caregiver of patient 12 is most likely preparing based on corresponding gesture(s). The one or more processors may compare information indicative of the amount or type of insulin dosage to a criteria of a proper insulin injection. As described herein, the criteria of a proper insulin injection may specify recommendations for the patent's diabetes therapy including recommended insulin dosage amount(s), insulin type(s), dosage schedule, whether sufficient time has elapsed between insulin injections, whether a meal is consumed between insulin injections, whether the patient is using basal or bolus insulin based on time of day, and/or the like. The criteria may further specify which insulin pen settings to activate in order to satisfy the above recommendations. If the criteria is not satisfied, the one or more processors may output an alert so that patient 12 or the caregiver of patient 12 does not inject patient 12 or, more generally, perform some modification to correct an impropriety associated with the insulin injection or increase the efficacy of the insulin injection.

To effectuate the generation of information indicative of amount of insulin and/or type of insulin dosage in the above-mentioned insulin injection, one or more processors 28 may leverage the data model for detecting the corresponding gesture(s). One example corresponding gesture to set insulin dosage amount and/or type may involve a number of clicks or amount of rotation on the insulin pen's dial. Another example corresponding gesture to set insulin dosage amount and/or type is to load a cartridge into the insulin pen or a similar injection device. One or more processors 28 increase an efficiency in detecting these gestures by way of a device confirmation and/or a patient confirmation. Another example corresponding gesture to set insulin dosage amount and/or type in a syringe is to intake, by suction, insulin into the syringe barrel. Other contextual cues may (in part) identify the insulin type, such as time of day and/or location. For example, long acting insulin may generally be delivered first thing in the morning or before bed in the evening, while rapid acting may generally be delivered before meals. Temporal and locational cues may discern between respective time periods where long or rapid acting insulins are more likely and proper.

Processing power and other resources are consumed while training and/or applying the data model to transform the user activity data into the detectable gestures. While one or more processors 28 may leverage the trained data model to distinguish insulin injections from other user activities described in the user activity data, even with training, structural and functional limitations may prevent the data model from rendering accurate predictions. Other limitations associated with inertial measurement unit(s) in wearable device 22 may further reduce the utility of the user activity data. While an example wearable device 22 (e.g., a smartwatch) housing one or more inertial measurement units may capture user activity data indicative of wrist and hand movements, these movements, however, may not accurately reflect the movement of the manual injection device for a number of reasons. It is possible for the patient to move, position, and/or orient the manual injection device without creating even a non-trivial amount of user activity data. It is possible for wearable device 22 to be on a different hand from the hand holding the manual injection device. As another limitation, a caretaker may administer the injection, resulting in no meaningful user activity data. In the wearable device's captured data, there is no mechanism to definitely identify patient or caregiver utilization of the manual injection device or any other injection device.

To minimize the above-mentioned inaccuracies in either the user activity data provided by wearable device 22 or in the data model and/or possibly reduce the resource requirement for the detection, one or more processors 28 may confirm (e.g., a confidence level for) the detected gestures using various datasets describing the patient or caregiver utilization of the manual injection device, injection device 30, or any other insulin delivery device. These datasets may be referred to herein as injection device data, examples of which include user input data provided via an input mechanism and/or sensor data provided by patient device 24, a network device of a cloud service, the insulin delivery device itself, and/or an external device to patient 12. In effect, confirmation of any detected gesture mitigates the above-mentioned limitations in wearable device 22.

When the detected gestures possibly identify (e.g., predict) an insulin injection, in response to the possible identification (e.g., prediction) of the insulin injection, some example devices, systems, and techniques of this disclosure further benefit patient 12 with example injection device data indicating at least a device confirmation or a patient confirmation. In a patient confirmation, patient 12 is presented with a query as to whether an insulin injection is about to occur or is occurring and by way of user input, patient 12 either confirms or denies a pending or recent occurrence of an insulin injection with any injection device embodiment including any manual injection device. In a device confirmation, one or more processors 28 confirm or reject the prediction with advantage of accurate data describing (e.g., user operation(s) of) the injection device including the manual injection device of FIG. 3.

For the manual injection device of FIG. 2, one or more processors 28 may be configured to confirm or reject predictions of insulin injections with the injection device data. Because the manual injection device may not be equipped with any sensing technology to assist in confirming or rejecting such predictions, one or more processors 28 leverage another source to access the injection device data. For some manual injection devices, one or more processors 28 may query the injection device data from patient device 24 or another device (e.g., smart cap attached to an insulin pen, a smart phone, and/or the like). For example, a smart phone may include sensing technology (e.g., an optical or electro-optical sensor, a combination of optical sensor and LED, an accelerometer, an ambient light sensor, a magnetometer, a gyroscope, a camera, and/or the like) to record example injection device data of a manual injection that has recently occurred.

One or more processors 28 may establish various criteria (e.g., standards, thresholds, conditions, etc.) for confirming the insulin injection prediction based upon user activity data provided by wearable device 22. Using an example set of criteria to confirm (or reject) any given prediction, one or more processors 28 may leverage injection device data, a more accurate information source, for evidence affirming the initial gesture detection based upon the user activity data provided by wearable device 22. Synthesizing the injection device data with the user activity data provides a complete picture of the patient's activities while utilizing any injection device. One example set of criteria may require only the above-mentioned vibration data while another example set of criteria may require both the vibration data. In addition (or as an alternative), one or more processors 28 may compare the user activity data with the injection device data for various indicia that the insulin injection did not occur and if sufficient indicia is identified in the comparison, reject the opposing prediction. It should be noted that machine learning concepts are incorporated into gesture detection, as described herein; for at least this reason, devices, systems, and techniques of this disclosure may avail themselves of established learning mechanisms to more accurately predict when an insulin injection is about to occur or is occurring, regardless of whether one or more processors 28 confirm or reject the predicted occurrence of a manual insulin injection. Some example learning mechanisms adjust the data model, for example, by adjusting an insulin injection definition using different gestures, by adjusting feature values or defining different features for a gesture, by adjusting the data model's prediction process (e.g., a mathematical function, a probability distribution, etc.), by adjusting the data model's metric or method for measuring user activities from data (e.g., accelerometer data) provided by wearable device 22, and/or by adjusting the data model in another manner.

Figure 3:
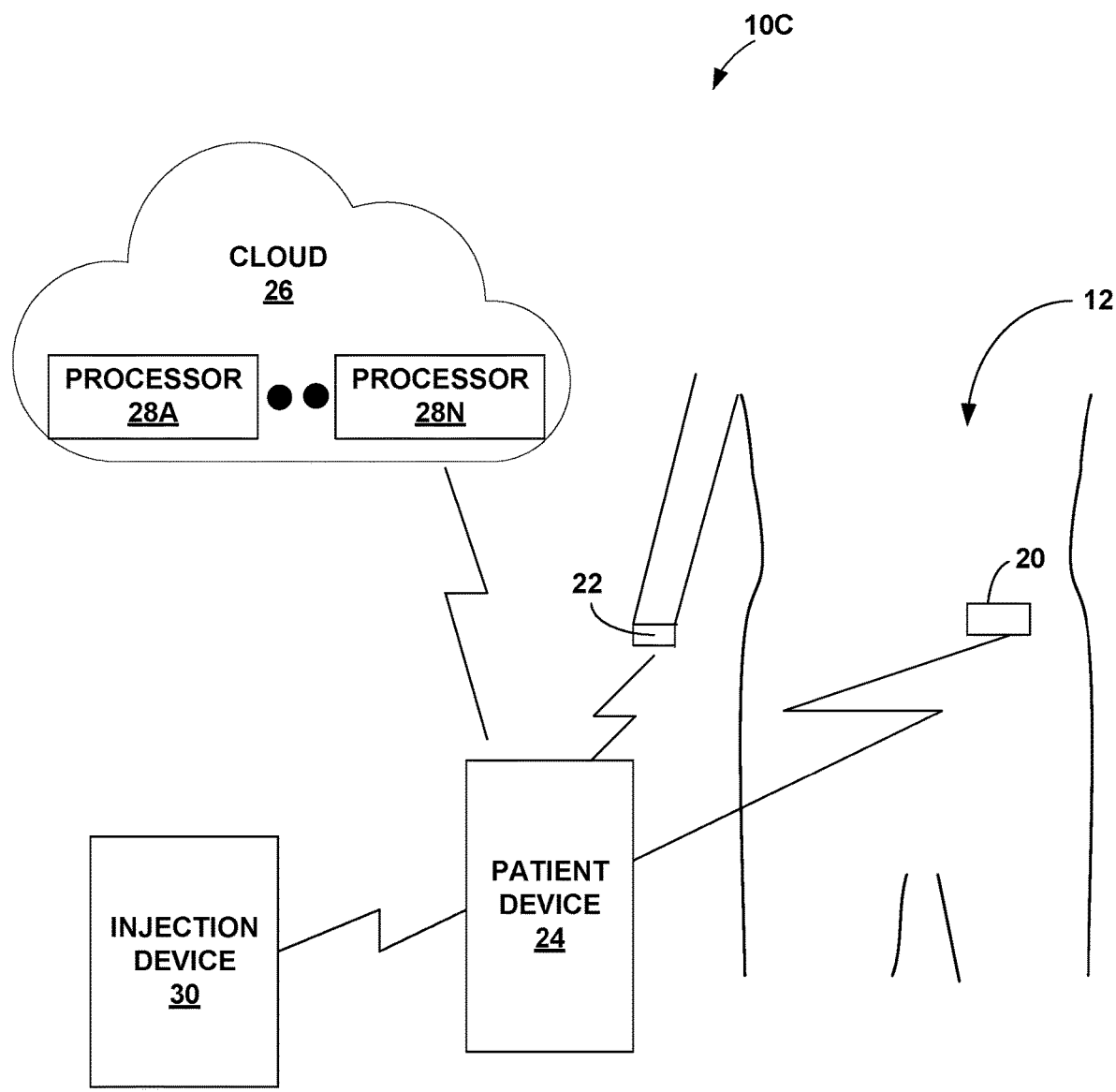
FIG. 3 is a block diagram illustrating another example system for delivering or guiding therapy dosage, in accordance with one or more examples described in this disclosure.

FIG. 3 is a block diagram illustrating another example system for delivering or guiding therapy dosage, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or possible a caretaker of patient 12) may utilize injection device 30 to inject himself or herself.

Injection device 30 may be different than a syringe because injection device 30 may be a device that can communicate with patient device 24 and/or other devices in system 10C. Also, injection device 30 may include a reservoir, and based on information indicative of how much therapy dosage to deliver may be able to dose out that much insulin for delivery. For example, injection device 30 may automatically set the amount of insulin based on the information received from patient device 24. In some examples, injection device 30 may be similar to insulin pump 14, but not worn by patient 12. One example of injection device 30 is an insulin pen, sometimes also called a smart insulin pen. Another example of injection device 30 may be an insulin pen with a smart cap, where the smart cap can be used to set particular doses of insulin.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be powered (e.g., battery powered) device, and the syringe may be device that requires no power.

To provide gesture-based control of diabetes therapy with an insulin delivery device (e.g., insulin pump 14, a syringe, and/or injection device 30), example techniques and systems implement data models that define certain user activities as gestures; examples of the defined gestures include groups (e.g., sequences) of gestures that when combined, form an example insulin injection with the insulin delivery device. One or more processors 28 of patient device 24 may detect data indicative of insulin injections by comparing user (e.g., patient) movement(s) and/or pose(s) of a defined insulin injection gesture in an example data model implementation with patient movement(s) and/or patient pose(s) corresponding to the gestures while patient 12 is holding the insulin delivery device.

For detecting gestures while patient 12 is in control of injection device 30, some example devices, systems, and techniques in this disclosure implement the same or similar data models used for detecting gestures while patient 12 is in control of a manual injection device. As one reason, user activity data generated to record gestures by a user (e.g., patient 12 or a caregiver of patient 12) while holding manual injection devices may be similar to user activity data generated to record gestures while the user (e.g., patient 12 or a caregiver of patient 12) is holding injection device 30. Even if the user activity data is somehow different (e.g., in a different format), substantially the same sensors are used to record movement and/or posture characteristics of the patient's arm and hand while utilizing (e.g., holding and operating) injection device 30. While there may be differences in how patient 12 performs a gesture to set an insulin dosage amount and/or type in injection device 30 as opposed to a syringe, those differences represent movement characteristics which may be codified as a definition for the specific gesture for injection device 30. For instance, instead of loading the syringe barrel with insulin, patient 12 is operating dials and other controls on injection device 30 to set a next insulin dosage amount and/or type. For at least these reasons, one or more processors 28 of patient device 24 may apply substantially the same data models to detect, in the user activity data generated from data provided by one or more (external) sensors in an external device such as wearable device 22, gestures (e.g., hand gestures) indicative of insulin injections with injection device 30.

Because the same external device, wearable device 22, operates as the source of the user activity data for both manual injection devices and examples of injections device 30, the same limitations may be present when predicting an occurrence of an insulin injection by injections device 30. To mitigation and/or eliminate some or all of these limitations, one or more processors 28 of patient device 24 may execute a mechanism configured to confirm or reject a prediction that the insulin injection is about to occur or is occurring. In some examples, one or more processors 28 of patient device 24 provide a device confirmation and/or a patient confirmation. In one example, one or more processors 28 of patient device 24 may communicate to injection device 30 a request to confirm or reject the prediction of the insulin injection by way of a device confirmation and/or a patient confirmation. In turn, injection device 30 communicates a response indicating a confirmation or a rejection based upon internal injection device data and/or input data from patient 12. If injection device 30 has been set to inject patient 12 or has already injected patient 12 and recorded the injection, injection device 30 responds the request with a positive device confirmation. On the other hand, if injection device 30 has not been set to inject patient 12 or has recently injected patient 12, injection device 30 responds the request with a negative device rejection. Injection device 30 may output an inquiry to patient 12 regarding whether that patient 12 is about to inject insulin and based upon input data provided by patient and indicative of patient 12's response, injection device 30 may respond to patient device 24 with a positive patient confirmation or a negative patient rejection (e.g., a denial). In an example device confirmation, one or more processors 28 of patient device 24 communicates to a communication component of injection device 30 a query for medical record data, including record data for any recent insulin injection. If a timestamp for a recent insulin injection matches a timestamp for the predication that the insulin injection is to occur, one or more processors 28 of patient device 24 may determine that injection device 30 is confirming the prediction of the occurrence of the insulin injection. In yet another example of a device confirmation, one or more processors 28 of patient device 24 may access an application programming interface provided by injection device 30 and invoke an interface function configured to provide a confirmation or a rejection of the predication of the insulin injection.

The above examples described insulin pump 14, a syringe, and injection device 30 as example ways in which to deliver insulin. In this disclosure, the term "insulin delivery device" may generally refer to a device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices or may be capable of dosing a particular amount of insulin. Injection device 30 may be powered (e.g., battery powered) device, and the syringe may be device that requires no power.

Figure 4:
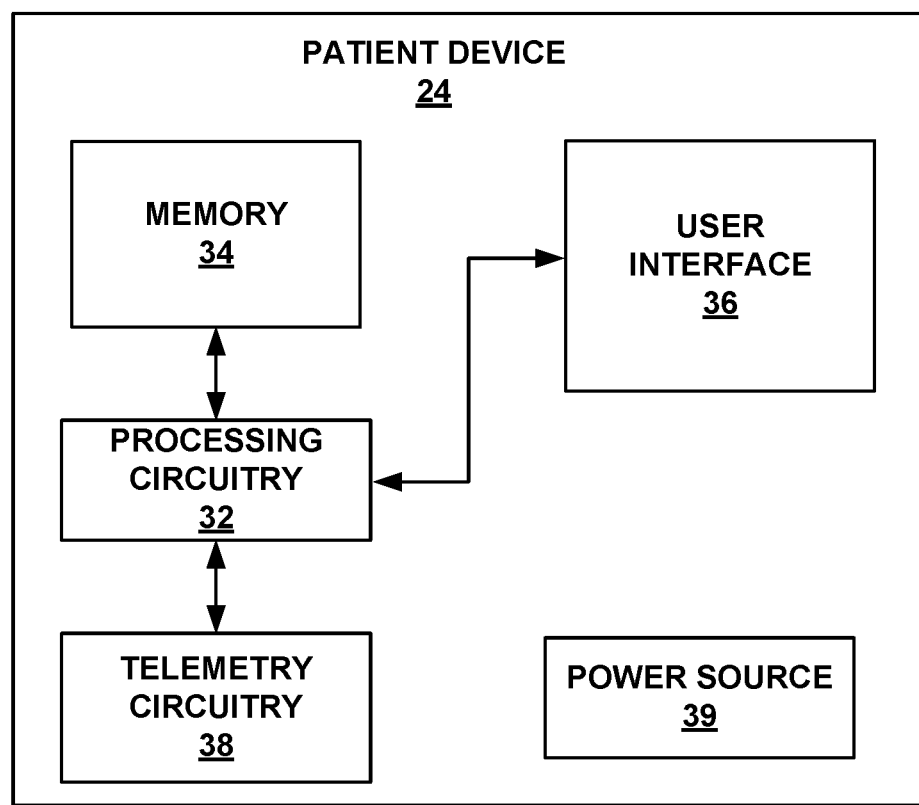
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, patient device 24 may be a notebook computer, a cell phone, or a workstation, for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be specialized controller for communicating with insulin pump 14, injection device 30, or a smart cap for a manual injection device.

Although the examples are described with one patient device 24, in some examples, patient device 24 may be a combination of different devices (e.g., mobile device and a controller). For instance, the mobile device may provide access to one or more processors 28 of cloud 26 through Wi-Fi or carrier network and the controller may provide access to insulin pump 14. In such examples, the mobile device and the controller may communicate with one another through Bluetooth or BLE. Various combinations of a mobile device and a controller together forming patient device 24 are possible and the example techniques should not be considered limited to any one particular configuration.

As illustrated in FIG. 4, patient device 24 may include a processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure.

In some examples, memory 34 of patient device 24 may store a plurality of parameters, such as amounts of insulin to deliver, target glucose level, time of delivery etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification to take insulin, amount of insulin, and time to take the insulin, via user interface 36.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a speaker for voice commands, and a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of food that patient 12 eats, such as for the initial learning phase, whether patient 12 took the insulin (e.g., through the syringe or injection device 30), and other such information.

Telemetry circuitry 38 includes any suitable hardware, firmware, software or any combination thereof for communicating with another device, such as cloud 26, insulin pump 14 or injection device 30, as applicable, wearable device 22, and sensor 20. Telemetry circuitry 38 may receive communication with the aid of an antenna, which may be internal and/or external to patient device 24. Telemetry circuitry 38 may be configured to communicate with another computing device via wireless communication techniques, or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24.

Prior to patient 12 or a caregiver of patient 12 injecting the insulin, there may be benefits in ensuring that the appropriate amount and/or correct type of insulin is going to be injected. As mentioned herein, there are a number of opportunities for a user of an insulin deliver device to administer an improper insulin injection. One or more processors of processing circuitry 32 or one or more processors 28 may access user activity data generated by one or more inertial measurement units and then, based upon the user activity data, generate information indicative of amount of insulin and/or type of insulin dosage in the insulin injection that patient 12 or the caregiver of patient 12 is most likely preparing based on corresponding gesture(s). One or more processors of processing circuitry 32 (or one or more processors 28) may identify a corresponding gesture based upon movement characteristics, posture characteristics, and other examples in the user activity data. Processing circuitry 32 (or one or more processors 28) may compare the information indicative of the amount or type of insulin dosage to a criteria of a proper insulin injection. As described herein, the criteria of a proper insulin injection may specify recommendations for the patent's diabetes therapy including recommended insulin dosage amount(s), insulin type(s), dosage schedule, whether sufficient time has elapsed between insulin injections, whether a meal is consumed between insulin injections, whether the patient is using basal or bolus insulin based on time of day, and/or the like. The criteria may further specify which insulin pen settings to activate in order to satisfy the above recommendations. The criteria may be determined by the patient, the caregiver, or any medical professional with authority over patient device 24 or cloud 26. The purpose of comparing information describing the time, amount and/or type set for a pending insulin injection to the criteria of a proper insulin injection is to protect the patient from injections of an incorrect amount and/or type of insulin and/or at an incorrect time. Consequences from improper insulin injections may range from minor discomfort to major declination in patient health. For example, if not enough time elapsed between a previous insulin injection and a current insulin injection, there is a possibility that the patient simply forgot about the previous insulin injection. If patient 12 did not eat any food between injections, the patient may end up with low glucose level.

If the criteria is not satisfied, processing circuitry 32 may output an alert so that patient 12 or the caregiver of patient 12 does not inject patient 12 or, more generally, perform some modification to correct an impropriety associated with the insulin injection or increase the efficacy of the insulin injection. In some examples, one or more processors 28 communicates to patient device 28 instructions directing patient device 28 to output the alert.

Figure 5:
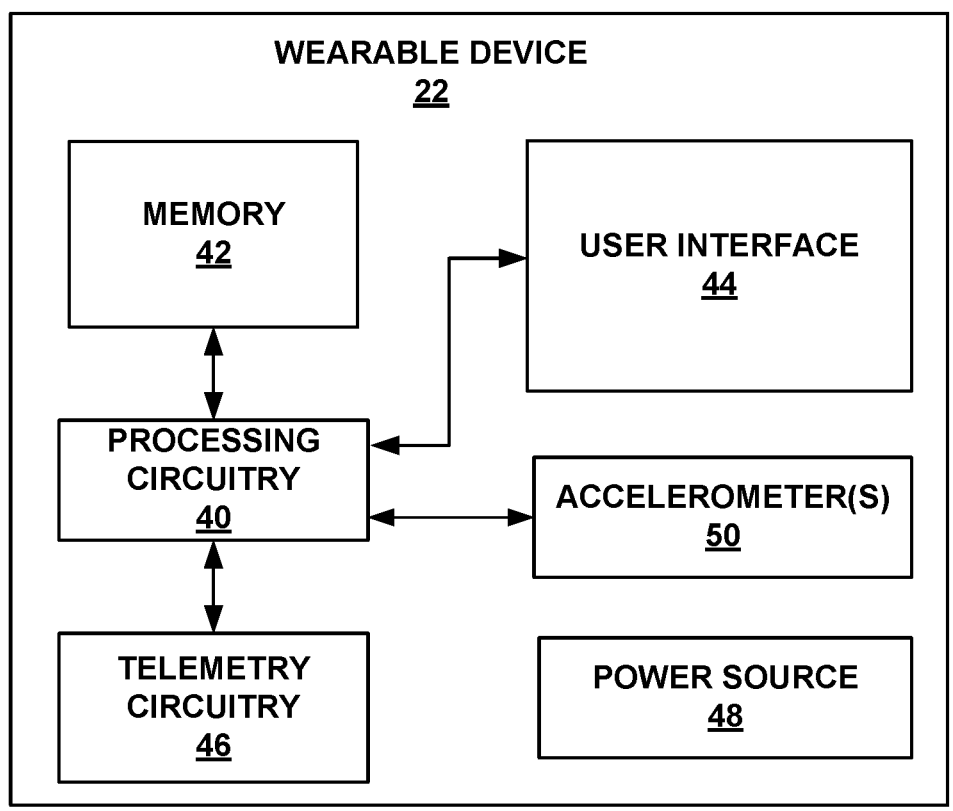
FIG. 5 is a block diagram illustrating an example of a wearable device, in accordance with one or more examples described in this disclosure.

FIG. 5 is a block diagram illustrating an example of a wearable device, in accordance with one or more examples described in this disclosure. As illustrated, wearable device 22 includes processing circuitry 40, memory 42, user interface 44, telemetry circuitry 46, power source 48, and inertial measurement units 50. Processing circuitry 40, memory 42, user interface 44, telemetry circuitry 46, and power source 48 may be similar to processing circuitry 32, memory 34, user interface 36, telemetry circuitry 38, and power source 39 of FIG. 3, respectively.

Inertial measurement units 50 may include gyroscopes and/or various components to determine a pitch-roll-yaw, and x-y-z coordinate of wearable device 22. In some examples, inertial measurement units 50 may be considered as a six-axis inertial measurement unit. For example, inertial measurement units 50 may couple a 3-axis accelerometer with a 3-axis gyroscope. The accelerometer may measure linear acceleration, while the gyroscope may measure rotational motion. Processing circuitry 40 may be configured to determine one or more movement characteristics based on values from inertial measurement units 50. For example, processing circuitry 40 may determine based on values from inertial measurement units 50 if patient 12 is moving his or her arm upwards, downwards, leftwards, rightwards, forwards, backwards, or some combination, including values related to frequency, amplitude, trajectory, position, velocity, acceleration, and/or pattern of movement. Processing circuitry 40 may determine based on values from inertial measurement units 50 orientation of the arm of patient 12, such as whether the back of the hand or the front of the hand is facing patient 12, or if a side of the hand is facing patient 12, such that the thumb is facing patient 12 and the side of the index finger is visible.

As one example, when patient 12 is holding chopsticks to eat, patient 12 may orient his or her wrist in a particular manner, which may be different than if patient 12 is holding a sandwich. The frequency of patient 12 moving his or her arm from a position where he or she is reaching food to a position where he or she is placing food in mouth may be different for different types of food. For example, the frequency and pattern of movement of eating with a fork may be different than eating with a spoon or a knife and fork, which may be different than eating with hands, like a sandwich or pizza. For all of these different food items, there may be a difference in the movement characteristics, and different output values from inertial measurement units 50. However, for all of the movement characteristics, one or more processors (including processing circuitry 40 in some examples) may be configured to determine that patient 12 is eating.

One or more inertial measurement units 50 may output such information (e.g., pitch-roll-yaw and x-y-z coordinates) of the arm of patient 12 to processing circuitry 40. Telemetry circuitry 46 may then output the information from processing circuitry 40 to patient device 24. Patient device 24 may forward the information to one or more processors 28 that can use the information to determine if patient 12 is eating (e.g., if a meal event is occurring).

To effectuate detection of gestures corresponding to an insulin injection by patient 12, inertial measurement units 50 may generate, for output, various data (e.g., pitch-roll-yaw and x-y-z coordinates) indicative of patient 12's activities including patient utilization of injection device 30, a manual injection device, or any other device configured to deliver a diabetes therapy. The data generated by inertial measurement units 50 (e.g., accelerometer data) may be processed into user activity data indicative of patient movement(s) and/or patient pose(s) corresponding the patient utilization with injection device 30. By comparing the user activity data to a data model configured to define gestures corresponding to the insulin injection, one or more processors 28 of the patient device 24 may detect one or more of these gestures and in response to that detection, determine whether to predict an occurrence of the insulin injection.

If patient 12 is using a manual injection device, additional sensors provide manual injection data to confirm the prediction. If patient 12 is using injection device 30, instead of having to use additional sensors and other hardware/software components to acquire manual injection device data, one or more processors 28 establishes a communication channel with injection device 30 and receives (e.g., by request) data describing operational details of one or more historical insulin injections. In this manner, the prediction that the insulin injection is to occur or is occurring may be confirmed or rejected by the injection device data for the manual injection device or injection device 30.

While the above example techniques may be beneficial in patient 12 receiving insulin at the right time, this disclosure describes example techniques to further proactively control delivery of insulin to patient 12. In particular, this disclosure describes example techniques to control deliverance of therapy to a diabetes patient where the therapy involves timely injections of an effective amount of a correct type of insulin. To effectuate these techniques, one or more processors 28 may determine whether an insulin injection that is about to occur is proper or improper for patient 12 by comparing various injection parameters to established criteria. As demonstrated above, the established criteria may include recommended and/or effective values/classifications for injection parameters including insulin dosage amount, insulin type, and/or injection schedule/time (or alternatively, a time interval between injections). Some techniques employ additional parameters and/or different parameters including an injection site/area, trajectory, and/or the like.

Once confirmed and deemed proper, record data for the insulin injection is stored and that record time may include a time for the injection. Ensuring timely injections of insulin prevents patient 12 from having low glucose levels in the blood. The same data model is applied continuously to user activity data over time, and when a subsequent insulin injection is detected, a time of that detection is compared to the recorded time of the previous injection. If a time difference falls below a recommended time interval between proper insulin injections (i.e., too early), patient device 24 outputs an alert warning patient 12 with textual and/or audio output. For example, if patient 12 is preparing an insulin injection but an insufficient amount of time elapsed from a previous insulin injection, there is a possibility that patient 12 forgot about the previous insulin injection and if patient 12 is not prevented from receiving a dose prematurely, excess insulin may build up in patient 12's bloodstream causing cells in patient 12's body to absorb too much glucose from the blood and/or patient 12's liver to release less glucose (i.e., Hypoglycemia). These two effects are exemplary of the consequences of improper insulin injections.

Meal events, depending on context, may or may not cause low glucose levels in patient 12's blood. If no meal is detected between insulin injections, patient 12 may end up with low glucose level, even if the subsequent insulin injection is timely. This correlation holds in some instances where patient 12 does not even receive the subsequent insulin injection. Applying the above-mentioned data model continuously to the user activity data streamed from wearable device 22 may further ensure patient 12 ate something before the subsequent insulin injection. If one or more processors 28 (and/or one or more processors of patient device 24), based on the user activity data provided by wearable device 22, detect a meal event and the subsequent insulin injection at appropriate respective times, one or more processors 28 may generate record data acknowledging the diabetes therapy and then, store that record data as part of patient 12's medical history (i.e., medical record). On the other hand, if, after monitoring the user activity data provided by wearable device 22, one or more processors 28 (and/or the one or more processors of patient device 24) fail to detect a meal event before detecting the subsequent insulin injection, patient device 24 may output an alert notifying patient 12 (or a caregiver of patient 12) of a potential impropriety in that injection. In some examples, patient device 24 outputs data requesting that patient 12 not make the subsequent insulin injection at this time and/or eat before the injection. Patient device 24 may output data indicative of an inquiry for patient 12 to answer regarding whether or not that patient 12 ate a meal between injections.

Example reasons for injecting rapid acting insulin, a first insulin type, may be to compensate for carbohydrates or to correct for high blood sugar. When correcting for high blood sugar, a subsequent insulin dose may account for insulin-on-board from previous injections. If a dose is given while patient 12 has normal blood sugar, and one or more processors 28 fail to detect a meal within a certain time period, for example, 15 minutes, then one or more processors 28 may output an alert to remind patient 12 to eat something to account for insulin in that dose. If a dose is given to correct high blood sugar and that dose was given after a recent similar dose, then one or more processors 28 may output an alert notifying patient 12 (and/or patient 12's caregiver) of a possible overcompensation of high blood sugar. The alert may further suggest a need for the caregiver to monitor patient 12's blood sugar and/or for patient 12 to possibly eat something to prevent hypoglycemia.

Doses of long acting insulin, a second insulin type, are generally delivered once per day; however, it is possible for patient 12 to receive two long acting doses in a short period of time or at different part of the day (e.g., a first dose in the morning and a second dose in the evening). In some examples, one or more processors 28 may output an alert warning patient 12 before the second subsequent dose is given and with sufficient time to prevent that dosage. In other examples, if one or more processors 28 detect a proper injection followed by a subsequent injection of long acting insulin, one or more processors 28 may output an alert notifying patient 12 to monitor their blood sugar for possible lows over the next 12-24 hours.

While these alerts may, in effect, prevent patient 12 from consequences resulting from having insulin injections without a proper intervening meal event, some examples confer one or more processors 28 (and/or one or more processors of patient device 24) with more control over patient 12's injections. For instance, if injection device 30 is communicably coupled to one or more processors 28 (and/or one or more processors of patient device 24), one or more processors 28 (and/or one or more processors of patient device 24) may communicate instructions to injection device 30 for halting (or delaying) the subsequent insulin injection without first detecting the meal event. If no meal event is detected and patient 12 is preparing the subsequent insulin injection, one or more processors 28 (and/or one or more processors of patient device 24) may issue a command to lock injection device 30 in a non-operative state. This may be executed automatically in response to detecting the subsequent insulin injection without the meal event. In other examples, injection device 30 may automatically shut down operations by patient 12 after determining that patient 12 most likely did not eat anything before attempting the subsequent insulin injection.

Figure 6:
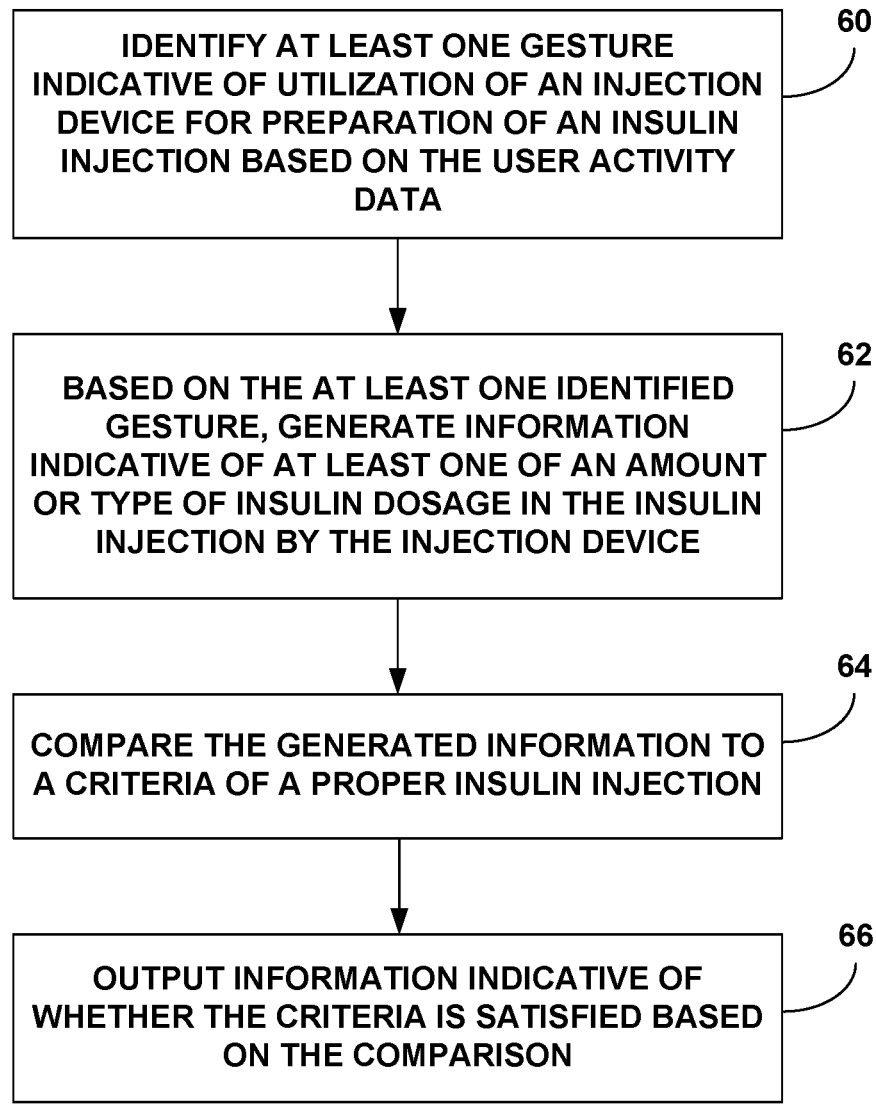
FIG. 6 is a flowchart illustrating an example method of operation, in accordance with one or more examples described in this disclosure.

FIG. 6 is a flowchart illustrating an example method of operation, in accordance with one or more examples described in this disclosure. FIG. 6 is described with respect to one or more processors. The one or more processors may be one or more processors 28, one or more processors of patient device 24 (e.g., processing circuitry 32), one or more processors of wearable device 22 (e.g., processing circuitry 40), one or more processors of insulin pump 14 (if available), or any combination thereof.

One or more processors may identify at least one gesture indicative of utilization of an injection device for preparation of an insulin injection based on the user activity data (60). The identification of the at least one gesture implies that an insulin injection (recently) occurred, is to occur, or is occurring. For example, the one or more processors may be a first set of one or more processors (e.g., one or more processors 28 on one or more servers of cloud 26) that receive data indicative of user activities including data indicative of gestures made by patient 12 or a caretaker of patient 12 while utilizing an injection device (e.g., injection device 30) in preparation of the insulin injection. An example insulin injection may consist of one or more gestures where each gesture is defined in accordance with a data model configured to distinguish insulin injections from other user activities (e.g., user activity or caregiver activity). In general, the present disclosure envisions user activities to include any activity by a user of the injection device. In one example, the data model includes a definition for each gesture of a plurality of gestures (e.g., user activity gestures) as well as a definition for each (detectable) example of an insulin injection by patient 12 as a combination of gestures. It is possible for a data model to define an example insulin injection as comprised of only one gesture.

The one or more processors may, based upon the at least one identified gesture, generate information indicative of at least one of an amount or a type of an insulin dosage in the insulin injection by the injection device (62). For example, an inertial measurement unit 50 within wearable device 22 provides one or more processors 28 vibration data associated with movements of dials and other instruments for setting the dosage amount and/or type. The one or more processors may compare the generated information to a criteria of a proper insulin injection (64). The criteria of the proper insulin injection includes any combination of a number of clicks used to set the insulin dosage, an amount of time that elapsed between insulin injections, whether the user consumed a meal between insulin injections, whether the patient is injecting with a basal insulin based on time of day, or whether the patient is injecting with a bolus insulin based on time of day. In some examples, the one or more processors determine whether the user consumed a meal based on user input and/or based on gesture data (e.g., as described above). The purpose of comparing information describing the time, amount and/or type set for a pending insulin injection to the criteria is to prevent the patient from being injected with an incorrect amount and/or type of insulin and/or at an incorrect time. Consequences from improper insulin injections may range from minor discomfort to major declination in patient health. For example, if not enough time elapsed between a previous insulin injection and a current insulin injection, there is a possibility that the patient simply forgot about the previous insulin injection. If patient 12 did not eat any food between injections, the patient may end up with low glucose level.

The one or more processors may output information indicative of whether the criteria is satisfied based on the comparison (66). In response to determining that the criteria of the proper insulin injection is not satisfied, the one or more processors may output an alert comprising at least one of text, graphics, sound, or video operative to notify the user of an improper insulin injection. The present disclosure envisions multiple scenarios in which the criteria of the proper insulin injection is not satisfied: Patient 12 receiving an insulin injection 1) without sufficient time elapsing after a previous injection, 2) without adequate food in the body, 3) without an effective dose (e.g., amount) of insulin, and/or 4) with an incorrect insulin type in the dose, among others. To illustrate by way of example, injections of rapid acting insulin, one type of insulin, may compensate for carbohydrates and/or correct for high blood sugar but when an insulin dose of rapid acting insulin undercompensates (e.g., too low in amount) or overcompensates (e.g., too high in amount), the one or more processors may output an alert notifying the user of the undercompensation or overcompensation, respectively. If the one or more processors fail to detect a meal within a certain time period, for example, fifteen minutes, the one or more processors may output an alert to remind patient 12 to eat something, for example, to account for the overcompensation of insulin. An alternative alert may suggest a subsequent insulin injection to correct for the undercompensation. An alert may be communicated to the caregiver's device, for example, prompting that caregiver to monitor patient 12's blood sugar, carbohydrates, and/or food intake.

In some examples, in response to a confirmation (e.g., device confirmation) of the insulin injection based upon injection device data, the one or more processors may generate at least one of: (1) for storage in a patient medical data, data recording the insulin injection, (2) for display on an electronic display, data indicative of an identification of insulin injection, or (3) for display on the electronic display, data indicative of an improper insulin injection when compared to the criteria of a proper insulin injection. The injection device data may be received from and communicated by a device (e.g., a smart cap for any insulin pen) communicably coupled to the injection device, a device (e.g., a smart phone) having sensors (e.g. an optical sensor) for sensing the injection device (e.g., a syringe), or the injection device itself.

One or more processors may process from patient 12 input data indicating a patient confirmation or a patient denial. In some examples, patient 12 communicates the input data as a response to a query submitted via a communication channel with patient device. Patient 12 may receive the query as content presented on an electronic display of a smart device or on an injection device. One or more processors, in response to a patient rejection of the insulin injection, may execute a learning technique to adjust the data model. In some examples, the learning technique adjusts the data model to more accurately predict insulin injections from gestures by patient 12 during operation of the injection device.

In some examples, the one or more processors may determine a time for a subsequent injection of insulin, determine whether the user is attempting to use the injection device to inject insulin based on movement detected by the wearable device prior to the time for the subsequent injection of insulin, and output data presenting an alert to the user that the user had already injected insulin based on the determination that the patient is attempting to use the injection device to inject insulin prior to the time for the subsequent injection of insulin.

Figure 7A:
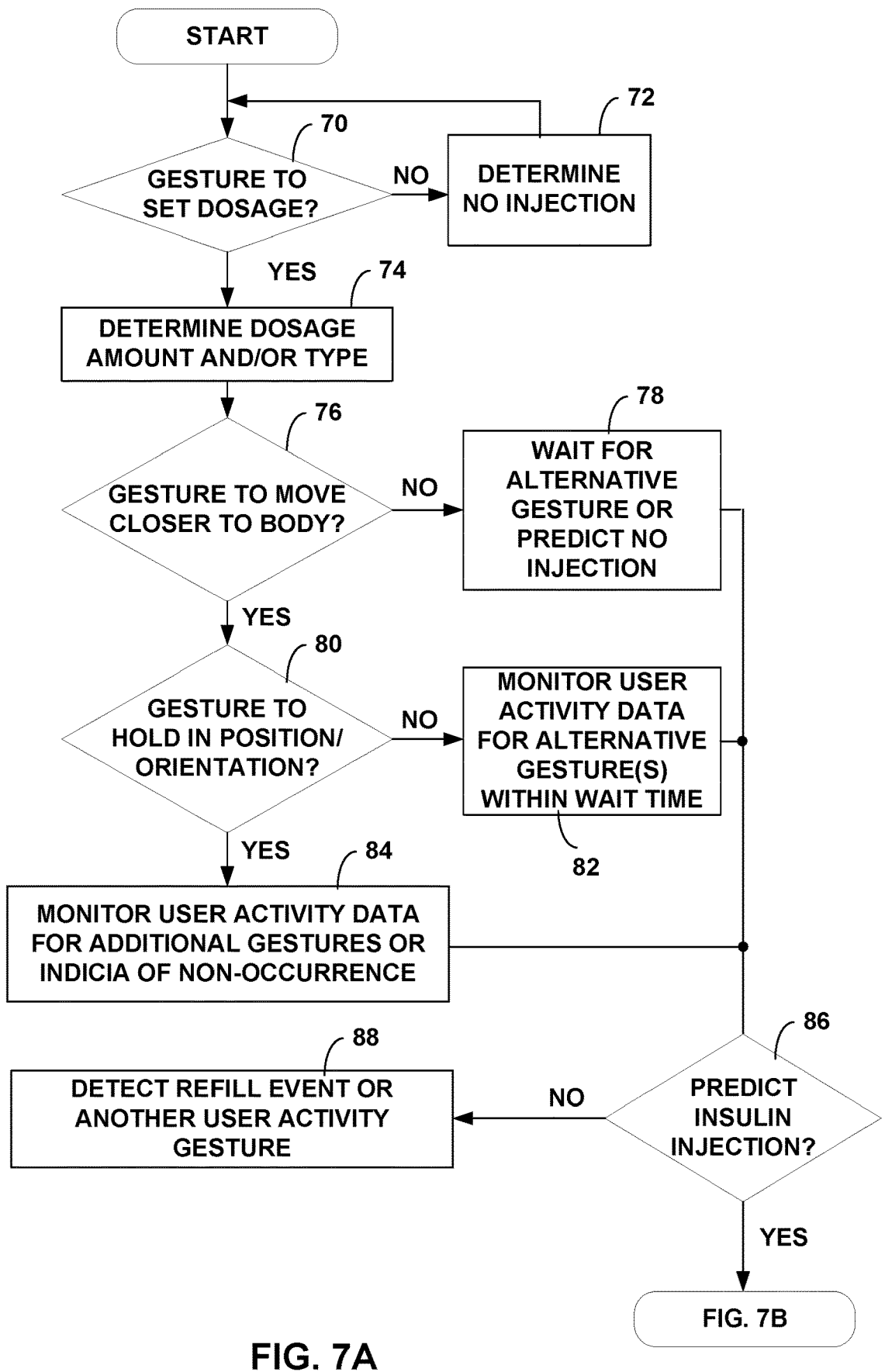
FIGS. 7A and 7B are flowcharts illustrating another example method of operation, in accordance with one or more examples described in this disclosure.
Figure 7B:
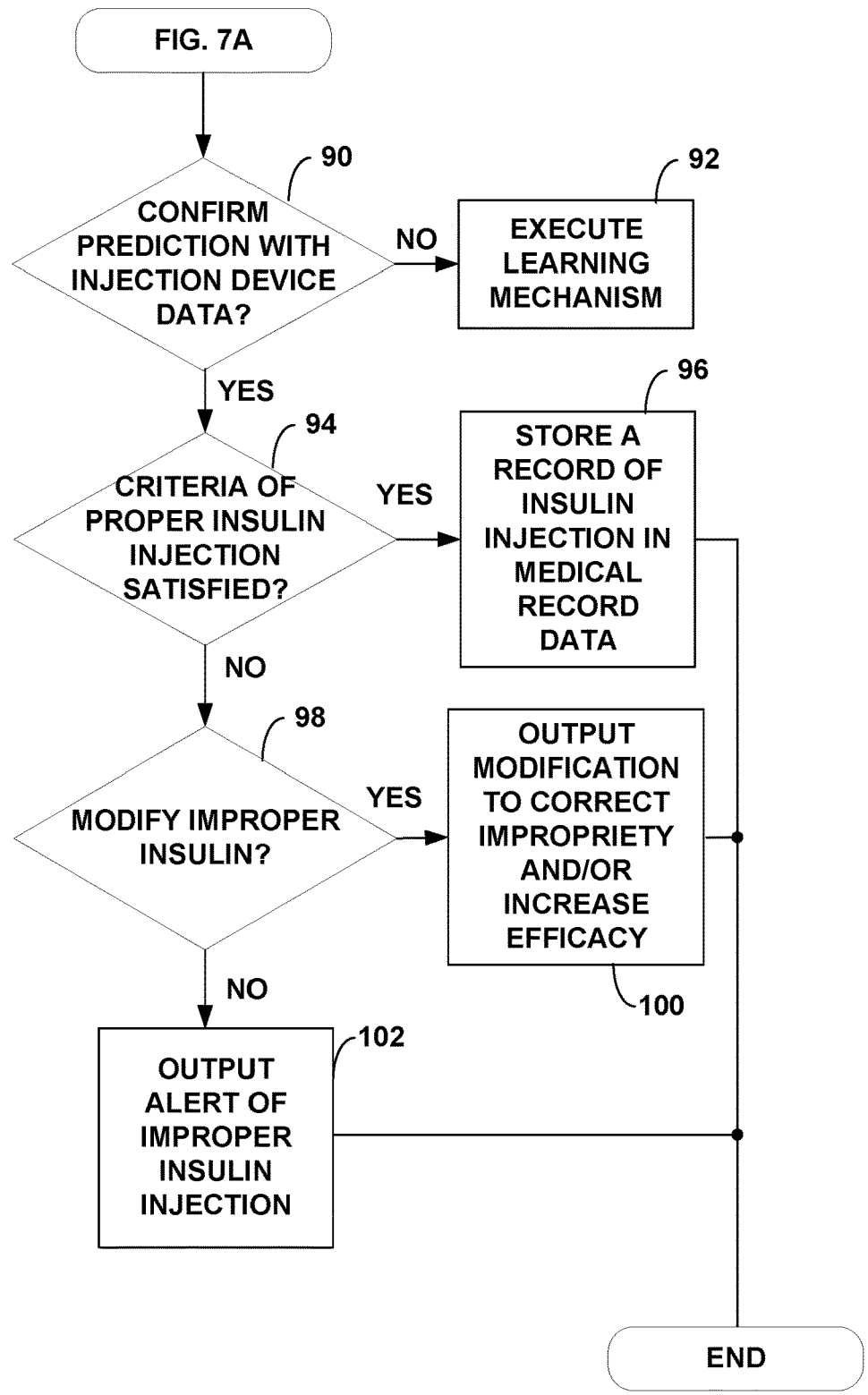

FIGS. 7A and 7B are flowcharts illustrating another example method of operation, in accordance with one or more examples described in this disclosure. Similar to FIG. 6, FIGS. 7A and 7B are described with respect to one or more processors. The one or more processors may be one or more processors 28, one or more processors of patient device 24 (e.g., processing circuitry 32), one or more processors of wearable device 22 (e.g., processing circuitry 40), one or more processors of insulin pump 14 (if available), or any combination thereof.

As illustrated in FIG. 7A, one or more processors may predict (e.g., determine) whether an insulin injection is to occur or is occurring, for example, by identifying one or more gestures indicative of utilization of an injection device for preparation of the insulin injection based on the user activity data. For instance, the one or more processors may determine whether the insulin injection is to occur or is occurring based on a data model for a patient 12 where the data model is configured to distinguish insulin injections from other user activities (e.g., patient activities and/or caregiver activities). An example insulin injection may consist of multiple gestures where each gesture is defined in accordance with a data model configured to distinguish insulin injections from other user activities. In one example, the data model includes a definition for each gesture of a plurality of gestures (e.g., user activity gestures) as well as a definition for each (detectable) example of an insulin injection by patient 12 as a combination of gestures. It is possible for a data model to define an example insulin injection as comprised of only one gesture. If the one or more processors determine that the insulin injection is not to occur (i.e., a non-occurrence), there may be no change in user activity, and patient 12 may continue with other non-insulin injection gestures. As illustrated in FIG. 7A, while gestures are made immediately prior to and during the delivery of insulin (e.g., basal insulin (e.g., baseline therapy)) to patient 12, the one or more processors may continuously examine user activity data to identify defined gestures corresponding to an example insulin injection and determine (e.g., predict) that an insulin injection is to occur or is occurring.

As further illustrated in FIG. 7A, one or more processors may detect (e.g., determine) whether a component insulin injection gesture such as a gesture to set a dosage is to occur or is occurring (70). For instance, the one or more processors may determine whether the any gesture, including the above-mentioned component insulin injection gesture, is to occur or is occurring based on user activity data indicating one or more movement characteristics, posture characteristics (e.g., position and/or orientation), and other characteristics detected by wearable device 22. These characteristics and other contextual information may be processed from sensor data generated by wearable device 22. If the one or more processors detect the gesture to set the dosage is to occur or is occurring (YES branch of 70), the one or more processors may determine a diabetes therapy dosage amount and/or type (74). For example, the one or more processors may determine an amount and/or a type of insulin dosage based upon data (e.g., vibration data) from an inertial measurement unit. If any of one of the insulin dosage amount, or a dosage type deviates from criteria indicating proper amount, dosage type, or time to deliver the insulin dosage, such a determination is postponed until after prediction and at least a device or patient confirmation. Such a postponement preserves resources and provides enough time to warn patient 12 and/or correct the insulin injection. If the one or more processors do not detect the gesture to set the dosage (NO branch of 70), the one or more processors may determine that an insulin injection has not been prepared or is not about to occur.

The one or more processors may detect (e.g., determine) whether a gesture to move the injection device closer to patient 12 body, another component insulin injection gesture, is to occur or is occurring (76). Similar to other gestures, the gesture to move the injection device close to patient 12 body may be detected if user activity data comprising patient movement characteristics and/or patient pose characteristics matches the data model's definition of the gesture. If the one or more processors fail to detect, in the user activity data (or other contextual data), the gesture to move the injection device closer to patient 12 body (NO branch of 76), the one or more processors may wait for alternative gesture or predict no injection after a suitable wait time (78). If the one or more processors detect that the gesture to move the injection device closer to patient 12 body is to occur or is occurring (YES branch of 76), the one or more processors may proceed to detect (e.g., determine) whether a gesture to hold the injection device in specific position/orientation, another gesture corresponding to the insulin injection, is set to occur or is occurring (80).

If the one or more processors do not detect, in the user activity data (or other contextual data), the above-mentioned gesture to hold the injection device (NO branch of 80), the one or more processors may monitor the user activity data for alternative gestures corresponding to the insulin injection within a wait time (82). In some examples, the wait time cannot exceed an amount of time consumed to administer an insulin injection.

If the one or more processors do detect the gesture to hold the injection device in a specific position/orientation (YES branch of 80), the one or more processors monitor the user activity data for additional gestures and/or indicia of non-occurrence within a wait time (84). The one or more processors may identify the above mentioned gestures corresponding to the insulin injection but there may be indication indicators there may be user activity data indicative of patient movements and/or patient pose contradicting a prediction of the insulin injection. For example, if there is no insulin in the injection device, the above-mentioned gestures cannot correspond to actual injection. If certain additional gestures are detected where those gestures also correspond to insulin injections (e.g., a gesture to clear the insulin of air bubbles), that detection counters any identification of indicia of non-occurrence.

The one or more processors may determine whether to predict the insulin injection is to occur or is occurring based upon the detection of the above-mentioned gestures, which are components of a composite insulin injection gesture, and any indicia of non-occurrence for the insulin injection gesture (86). If the one or more processors predict an occurrence of the insulin injection (YES branch of 86), the one or more processors proceed to FIG. 7B. If the one or more processors cannot predict an occurrence of the insulin injection (NO branch of 86), the one or more processors detect a refill event or another user activity gesture instead of the insulin injection (88). For example, if sufficient indicia of non-occurrence are identified based upon the user activity data, the one or more processors may determine that the above-mentioned detection of the component insulin injection gestures was a false positive. One example of sufficient indicia of non-occurrence is a refill event where injection 30 is refilled with another cartridge of insulin. Another example of sufficient indicia of non-occurrence is recent patient 12 activity without the injection device.

If injection device 30 is not available, then patient 12 may utilize a syringe to deliver the partial therapy dosage. For example, the one or more processors may output information to patient device 24 for the insulin dosage and/or type, and patient 12 may then use the syringe to deliver the partial therapy dosage based on the information that patient device 24 outputs via user interface 36.

Turning to FIG. 7B, after the one or more processors predict the pending diabetes therapy in the form of an insulin injection, the one or more processors may confirm the prediction that the insulin injection is to occur or is occurring (86).

For instance, the one or more processors may predict (e.g., determine) whether the insulin injection is to occur or is occurring based on one or more movement characteristics, pose characteristics (e.g., position and/or orientation), and other characteristics detected by wearable device 22. These characteristics and other contextual information may be acquired/captured (and then, processed) into user activity data and compared with a data model defining each gesture corresponding to example insulin injections.

If, following FIG. 7A, the one or more processors predict that the insulin injection is to occur or is occurring, the one or more processors execute a mechanism to confirm or reject the prediction based upon injection device data (90). If the prediction of an occurrence of the insulin injection cannot be confirmed and/or is rejected (NO branch of 90), then the one or more processors may execute a machine learning mechanism to adjust the data model to more accurately predict no injection (i.e., a non-occurrence) for the captured user activity data and for insulin injections in general (92). If addition, the one or more processors may continue monitoring the user activity data for insulin injections.

If the prediction of an occurrence of the insulin injection is confirmed (YES branch of 90), the one or more processors may determine whether criteria of a proper insulin injection are satisfied (94). For example, the one or more processors may apply each criterion to parameters of the predicted insulin injection to determine satisfaction or non-satisfaction. Such parameters include insulin dosage amount, insulin type, injection time, and/or the like. The criteria, therefore, includes correct (e.g., recommended and/or effective) versions of the same parameters and if an insufficient number of criterion is satisfied, the one or more processors may identify an improper insulin injection is to occur or is occurring. These parameters may be determined from the user activity data and the insulin injection data to the prediction. The criteria may be pre-determined or learned over time.

If the criteria are satisfied (YES branch of 94), then the one or more processors may store a record of the pending insulin injection in medical record data (96). The one or more processors may wait until the device or patient confirmation before storing the medical record data.

If the criteria are not satisfied (NO branch of 94), then the one or more processors may determine whether to modify the pending improper insulin injection (98). In some examples, if the one or more processors determine that the pending improper insulin injection is to be modified (YES branch of 98), the one or more processors may output, on an electronic display for patient device 24, various information to patient device 24 and/or injection device 30; one example of the outputted information includes information (e.g., content) describing a modification to correct an impropriety and/or increase efficacy in the pending insulin injection (100). In some examples, the electronic display may be included in user interface 36 of patient device 24. The one or more processors may output, on the electronic display, a correct insulin dosage amount and/or insulin dosage type in an attempt to modify the pending improper insulin dosage amount and/or type, respectively. In some examples, the one or more processors (e.g., in patient device 24 or a network server in cloud 26) may output data directing injection device 30 to automatically correct the insulin dosage amount and/or insulin dosage type or prevent insulin injection from occurring. The one or more processors may output a recommended and/or effective orientation/position to hold injection device 30 or the manual injection device before administering the insulin.

As another example, the one or more processors may output information for patient 12 or a caregiver of patient 12 to follow where the output information may include a set of instructions for properly administering the diabetes therapy to the patient. The set of instructions may indicate a correct insulin type, an appropriate dose of the correct insulin type, a safe injection area to receive the appropriate dose of the correct insulin type, a recommend trajectory when motioning the injection device to inject the appropriate dose of the correct insulin, an orientation or a position to hold the injection device before following the recommended trajectory to the safe injection area (e.g., site), injection time (or window of time), and/or a time interval between insulin injections. The one or more processors may output, on the electronic display of user interface 36, data comprising a graphical representation of a proper insulin injection. In some examples, the one or more processors of patient device 24 communicate, to a device maintained by a caregiver for the patient, data indicative of content presenting the set of instructions and/or the graphical representation. To assist the caregiver's administration of the diabetes therapy, the graphical representation and/or the set of instructions may be displayed, as output, on an electronic display of the device maintained by the caregiver.

If the one or more processors determine not to modify the improper insulin injection (NO branch of 98), the one or more processors output an alert of the improper insulin injection (102). In response to determining that the insulin injection does not to satisfy the criteria of the proper insulin injection, the one or more processors may output, on the electronic display of patient device 24, any combination of text, graphics, sound, video, and/or other content types in an alert operative to notify patient 12 of the improper insulin injection. If, for example, the one or more processors determine that preventing or delaying the improper insulin injection is more beneficial than modifying the injection, the one or more processors may output such an alert to notify patient 12 of the improper insulin injection. For example, if a current time does not comply with an injection schedule recommended for patient 12, then the injection is improper for being untimely and is to be prevented or delayed via the alert. The alert may include text as well as an audible warning. As another example, if sufficient time has not elapsed between a previous injection, then this the subsequent injection is improper and is to be prevented or delayed via the alert. In another example, patient device 24 or a network device on cloud 26 may communicate instructions directing injection device 30 to halt the pending improper insulin injection.

As described above, there may be various sensors used to measure different contextual information. The following provides some example ways in which the sensor information may be utilized. For example, based on movement characteristics, one or more processors 28 may determine how much and when to deliver insulin. In some examples, one or more processors 28 may withhold prompts to patient 12, such as low battery, or other types of alerts like if glucose is slightly out of range, based on the sensor data, such as withhold prompts if patient 12 is driving or sleeping. The sensors may indicate changes in temperature, and one or more processors 28 may set the target glucose level based on the temperature. The sensors may indicate with patient 12 is exercising, and one or more processors 28 may set target glucose levels based on if patient 12 is exercising, and if patient 12 is performing aerobic or anerobic exercises.

In some examples, when patient device 24 and/or wearable device 22 output information (e.g., broadcast) to one or more processors 28 may be based on contextual information of patient 12, such as biometrics, location, and time of day. In some examples, patient device 24 and/or wearable device 22 may output information in a way that conserves power (e.g., broadcasting during sleep can be reduced).

There may be other ways in which to utilize information of location of patient 12 to assist with controlling glucose levels. As one example, patient device 24 may, based on the location of patient 12 being that patient 12 is at a grocery store, output information of foods or food companies that provide product that helps treat diabetes.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for controlling delivery of therapy for diabetes, the system comprising:
   a wearable device configured to generate user activity data associated with an arm of a user; and
   one or more processors configured to:
      identify at least one gesture indicative of utilization of an injection device for preparation of an insulin injection based on the user activity data;
      based on the at least one identified gesture, generate information indicative of at least one of an amount or type of insulin dosage in the insulin injection by the injection device;
      compare the generated information to a criteria of a proper insulin injection; and
      output information indicative of whether the criteria is satisfied based on the comparison.

2. The system of claim 1, wherein to identify the at least one gesture, the one or more processors are configured to:
   identify, based on the user activity data, at least one of (1) a first gesture to set at least one of the amount or the type of the dosage in the insulin injection, (2) a second gesture to move the injection device closer to a patient body, or (3) a third gesture to hold the injection device at a specific position or a specific orientation.

3. The system of claim 1, wherein the criteria of the proper insulin injection comprises one or more of: a number of clicks used to set the amount of the insulin dosage, an amount of time that elapsed between insulin injections, whether the user consumed a meal between insulin injections, whether the patient is being injected with a basal insulin based on time of day, or whether the patient is being injected with a bolus insulin based on time of day.

4. The system of claim 1, wherein to output information indicative of whether the criteria is satisfied, the one or more processors are configured to:
   in response to determining that the criteria of the proper insulin injection is not satisfied, output an alert comprising at least one of text, graphics, sound, or video operative to notify the user of an improper insulin injection.

5. The system of claim 1, wherein the wearable device comprises:
   one or more inertial measurement units to generate at least a portion of the user activity data.

6. The system of claim 1, wherein the one or more processors are configured to:
   receive, from at least one of the injection device, a device communicably coupled to the injection device, or a device having sensors for sensing the injection device, a confirmation of the insulin injection.

7. The system of claim 1, further comprising a patient device, wherein the patient device includes the one or more processors.

8. The system of claim 1, wherein the one or more processors are further configured to:
   determine a time for a subsequent injection of insulin;
   determine whether the user is attempting to use the injection device to inject insulin based on movement detected by the wearable device prior to the time for the subsequent injection of insulin; and output data presenting an alert to the user that the user had already injected insulin based on the determination that the patient is attempting to use the injection device to inject insulin prior to the time for the subsequent injection of insulin.

9. The system of claim 1, wherein the one or more processors are further configured to:
output data indicative of a modification to correct an impropriety associated with the insulin injection or increase an efficacy of the insulin injection based on the comparison indicating that the criteria is not satisfied.

10. The system of claim 1, wherein the one or more processors are further configured to:
output data directing the injection device to automatically modify the insulin injection or prevent the insulin injection based on the comparison indicating that the criteria is not satisfied.

11. The system of claim 1, wherein the one or more processors are further configured to:
generate data presenting a set of instructions for properly administering the therapy to a patient, the set of instructions indicating a correct insulin type, an appropriate dose of the correct insulin type, a safe injection area to receive the appropriate dose of the correct insulin type, a recommend trajectory when motioning the injection device to inject the appropriate dose of the correct insulin type, an orientation or a position to hold the injection device before following the recommended trajectory to the safe injection area, and a time interval between insulin injections.

12. The system of claim 11, wherein the one or more processors is further configured to:
communicate, to a device maintained by a caregiver for the patient, the data presenting the set of instructions, wherein the set of instructions are displayed, as output, on an electronic display of the device maintained by the caregiver.

13. A method comprising:
identifying, by one or more processors, at least one gesture indicative of utilization of an injection device for preparation of an insulin injection based on user activity data, wherein a wearable device is configured to generate the user activity data associated with an arm of a user;
based on the at least one identified gesture, generating, by the one or more processors, information indicative of at least one of an amount or type of insulin dosage in the insulin injection by the injection device;
comparing, by the one or more processors, the generated information to a criteria of a proper insulin injection; and
outputting, by the one or more processors, information indicative of whether the criteria is satisfied based on the comparison.

14. The method of claim 13, wherein identifying the at least one gesture further comprises:
identifying, based on the user activity data, at least one of (1) a first gesture to set at least one of the amount or the type of the dosage in the insulin injection, (2) a second gesture to move the injection device closer to a patient body, or (3) a third gesture to hold the injection device at a specific position or a specific orientation.

15. The method of claim 13, wherein the criteria of the proper insulin injection comprises one or more of: a number of clicks used to set the insulin dosage, an amount of time that elapsed between insulin injections, whether the user consumed a meal between insulin injections, whether the patient is injecting with a basal insulin based on time of day, or whether the patient is injecting with a bolus insulin based on time of day.

16. The method of claim 13, wherein outputting the information indicative of whether the criteria is satisfied further comprises:
in response to determining that the criteria of the proper insulin injection is not satisfied, outputting an alert comprising at least one of text, graphics, sound, or video operative to notify the user of an improper insulin injection.

17. The method of claim 13 further comprising:
receiving, from at least one of the injection device, a device communicably coupled to the injection device, or a device having sensors for sensing the injection device, a confirmation of the insulin injection.

18. The method of claim 13 further comprising:
determining a time for a subsequent injection of insulin;
determining whether the user is attempting to use the injection device to inject insulin based on movement detected by the wearable device prior to the time for the subsequent injection of insulin; and
outputting data presenting an alert to the user that the user had already injected insulin based on the determination that the patient is attempting to use the injection device to inject insulin prior to the time for the subsequent injection of insulin.

19. The method of claim 13 further comprising:
outputting data indicative of a modification to correct an impropriety associated with the insulin injection or increase an efficacy of the insulin injection based on the comparison indicating that the criteria is not satisfied.

20. A computer-readable storage medium storing instructions thereon that when executed cause one or more processors to:
identify at least one gesture indicative of utilization of an injection device for preparation of an insulin injection based on user activity data, wherein a wearable device is configured to generate the user activity data associated with an arm of a user;
based on the at least one identified gesture, generate information indicative of at least one of an amount or type of insulin dosage in the insulin injection by the injection device;
compare the generated information to a criteria of a proper insulin injection; and
output information indicative of whether the criteria is satisfied based on the comparison.

* * * * *